(12) United States Patent
Melo et al.

(10) Patent No.: US 7,718,845 B2
(45) Date of Patent: *May 18, 2010

(54) PRODUCTION OF GROWTH HORMONE IN THE MILK OF A TRANSGENIC BOVINE AND METHODS OF PURIFICATION OF THE GROWTH HORMONE FROM THE MILK

(75) Inventors: Carlos Alberto Melo, Prov. de Buenos Aires (AR); Lino Baranao, Ciudad de Buenos Aires (AR); Cesar Horacio Carbonetto, Ciudad de Buenos Aires (AR)

(73) Assignee: Sterrenbeld Biotechnologie North America, Inc., Wilmington, DE (US)

( * ) Notice: Subject to any disclaimer, the term of this patent is extended or adjusted under 35 U.S.C. 154(b) by 643 days.

This patent is subject to a terminal disclaimer.

(21) Appl. No.: 10/952,377

(22) Filed: Sep. 29, 2004

(65) Prior Publication Data

US 2005/0177879 A1    Aug. 11, 2005

Related U.S. Application Data

(60) Provisional application No. 60/556,026, filed on Mar. 25, 2004, provisional application No. 60/556,027, filed on Mar. 25, 2004, provisional application No. 60/506,735, filed on Sep. 30, 2003, provisional application No. 60/506,736, filed on Sep. 30, 2003.

(51) Int. Cl.
*A01K 67/027*    (2006.01)
*A23J 1/00*    (2006.01)

(52) U.S. Cl. ............... 800/7; 800/14; 800/24; 530/412; 530/413; 530/416; 530/417

(58) Field of Classification Search ............ 800/7, 800/14–18, 24
See application file for complete search history.

(56) References Cited

U.S. PATENT DOCUMENTS

| | | | |
|---|---|---|---|
| 4,371,462 A * | 2/1983 | Hecht | 530/399 |
| 5,741,957 A | 4/1998 | Deboer et al. | |
| 6,013,857 A * | 1/2000 | Deboer et al. | 800/15 |
| 6,395,958 B1 | 5/2002 | Strelchenko et al. | |
| 6,451,527 B1 | 9/2002 | Larocca et al. | |
| 7,105,314 B2 | 9/2006 | Kjeldsen | |
| 2002/0146779 A1 | 10/2002 | Cottingham et al. | |
| 2006/0179500 A1 | 8/2006 | Meade et al. | |
| 2008/0060089 A1 | 3/2008 | Melo et al. | |
| 2008/0229438 A1 | 9/2008 | Melo et al. | |

FOREIGN PATENT DOCUMENTS

| | | |
|---|---|---|
| WO | WO 91/03551 | 3/1991 |
| WO | WO 95/17085 | 6/1995 |
| WO | WO 99/51724 A1 | 10/1999 |

OTHER PUBLICATIONS

Schnieke et al. Human Factor IX Transgenic Sheep Produced by Transfer of Nuclei from Transfected Fetal Fibroblasts. Science. 1997, vol. 278, pp. 2130-2133.*
Henwood et al. Expanded Spectrum of Recombinant Human Growth Hormone Therapy. Current Opinion in Pediatrics. 2002, vol. 14, pp. 437-442.*
de Oliveira et al. High-Yield Purification of Biosynthetic Human Growth Hormone Secreted in *Escherichia coli* Periplasmic Space. Journal of Chromatography A. 1999, vol. 852, pp. 441-450.*
Ozyurt et al. Recovery of Antithrombin III from Milk by Expanded Bed Chromatography. Journal of Chromatography A. 2002, vol. 944, pp. 203-210.*
Fehilly et al. Cytogenetic and Blood Group Studies of Sheep/Goat Chimaeras. J. Reprod. Fertility. 1985, vol. 74, pp. 215-221.*
Meirelles et al. Complete Replacement of the Mitochondrial Genotype in a *Bos indicus* Calf Reconstructed by Nuclear Transfer to a *Bos taurus* Oocyte. Genetics 2001, vol. 158, pp. 351-356.*
Mitalipov et al. Rhesus Monkey Embryos Produced by Nuclear Transfer from Embryonic Blastomeres or Somatic Cells. Biol. Reprod. 2002, vol. 66, pp. 1367-1373.*
Simerly, C. et al. Molecular Correlates of Primate Nuclear Transfer Failures. Science. Apr. 11, 2003, vol. 300, p. 297.*
Salamone et al. High Levels of Expression of Bioactive Recombinant Growth Hormone in the Milk of a Cloned Transgenic Cow. Journal of Biotechnology. 2006, vol. 124, pp. 469-472.*
Baguisi, A., et al., "Production of goats by somatic cell nuclear transfer," *Nat. Biotechnol.* 17:456-461, Nature America Publishing (1999).
Campbell, K.H.S., et al., "Sheep cloned by nuclear transfer from a cultured cell line," *Nature* 380:64-66, Macmillan Magazines Ltd. (1996).

(Continued)

*Primary Examiner*—Deborah Crouch
(74) *Attorney, Agent, or Firm*—Sterne, Kessler, Goldstein & Fox P.L.L.C.

(57) ABSTRACT

The invention relates to a method of producing a protein of interest, comprising making a non-human transgenic mammal that produces said protein in its milk, obtaining said milk from the non-human transgenic mammal and purifying said protein of interest from the milk. Transgenic bovine animals were generated, which are able to produce human growth hormone in mammary glands. The method involves cloning of a genetic construct encoding hGH gene and beta casein promoter conveniently in an expression vector. It also includes transfection procedures into fetal bovine somatic cells, generally fibroblasts, and the nuclear transfer into enucleated bovine oocytes, generating thus transgenic embryos. The method also includes other procedures to generate transgenic embryos for the further expansion of the transgenic herd, such as the subcloning of transgenic female bovines, the superovulation of transgenic cows and their insemination with semen from a non-transgenic or a transgenic male bovine, and the superovulation of non-transgenic cows and their insemination with semen from a transgenic male bovine. Afterwards, transgenic embryos give rise to transgenic cattle that produce human growth hormone in huge amounts in their milk, from which the hormone is completely purified and analysed to fulfill all the requirements for the manufacture of a pure biopharmaceutical product.

34 Claims, 15 Drawing Sheets

OTHER PUBLICATIONS

Cheong, H-T., et al., "Birth of Mice after Transplantation of Early Cell-Cycle-Stage Embryonic Nuclei into Enucleated Oocytes," *Biol. Reprod.* 48:958-963, Academic Press (1993).

Cibelli, J.B., et al., "Cloned Transgenic Calves Produced from Nonquiescent Fetal Fibroblasts," *Science* 280:1256-1258, American Association for the Advancement of Science (1998).

Collas, P., and Robl, J.M., "Relationship between Nuclear Remodeling and Development in Nuclear Transplant Rabbit Embryos," *Biol. Reprod.* 45:455-465, Academic Press (1991).

Collas, P., et al., "Preparation of Nuclear Transplant Embryos by Electroportation," *Anal. Biochem.* 208:1-9, Academic Press (1993).

Kato, Y., et al., "Eight Calves Cloned from Somatic Cells of a Single Adult," *Science* 282:2095-2098, American Association for the Advancement of Science (1998).

Kwon, O.Y., and Kono, T., "Production of identical sextuplet mice by transferring metaphase nuclei from four-cell embryos," *Proc. Natl. Acad. Sci. U S A* 93:13010-13013, National Academy of Sciences (1996).

Liu, L., et al., "Nuclear Transfer in Sheep Embryos: The Effect of Cell-Cycle Coordination Between Nucleus and Cytoplasm and the Use of In Vitro Matured Oocytes," *Mol. Reprod. Dev.* 47:255-264, Wiley-Liss (1997).

Liu, L., et al., "Parthenogenetic Development and Protein Patterns of Newly Matured Bovine Oocytes After Chemical Activation," *Mol. Reprod. Dev.* 49:298-307, Wiley-Liss (1998).

McGrath, J., and Solter, D., "Nuclear and Cytoplasmic Transfer in Mammalian Embryos," in *Developmental Biology, A Comprehensive Synthesis*, vol. 4, *Manipulation of Mammalian Development*, Gwatkin, R.B.L., ed., Plenum Press, New York, NY, pp. 37-55 (1986).

Stice, S.L., and Keefer, C.L., "Multiple Generational Bovine Embryo Cloning," *Biol. Reprod.* 48:715-719, Academic Press (1993).

Tsunoda, Y., et al., "Cytogenetic analysis of reconstituted one-cell mouse embryos derived from nuclear transfer of fetal male germ cells," *J. Reprod. Fertil.* 96:275-281, Portland Press (1992).

Wakayama, T., et al., "Full-term development of mice from enucleated oocytes injected with cumulus cell nuclei," *Nature* 394:369-374, Macmillan Publishers Ltd. (1998).

Wells, D.N., et al., "Adult somatic cell nuclear transfer is used to preserve the last surviving cow of the Enderby Island cattle breed," *Reprod. Fertil. Dev.* 10:369-378, Commonwealth Scientific and Industrial Research Organization (1998).

Wells, D.N., et al., "Production of Cloned Calves Following Nuclear Transfer with Cultured Adult Mural Granulosa Cells," *Biol. Reprod.* 60:996-1005, Academic Press (1999).

Wells, D.N., et al., "Production of Cloned Lambs from an Established Embryonic Cell Line: A Comparison between In Vivo- and In Vitro-Matured Cytoplasts," *Biol. Reprod.* 57:385-393, Academic Press (1997).

Westhusin, M.E., et al., "Viable embryos and normal calves after nuclear transfer into Hoechst stained enucleated demi-oocytes of cows," *J. Reprod. Fertil.* 95:475-480, Portland Press (1992).

Willadsen, S.M., "Nuclear transplantation in sheep embryos," *Nature* 320:63-65, Macmillan Journals Ltd. (1986).

Wilmut, I., et al., "Viable offspring derived from fetal and adult mammalian cells," *Nature* 385:810-813, Macmillan Publishers Ltd. (1997).

Co-Pending U.S. Appl. No. 10/953,376, Melo et al., filed Sep. 29, 2004 (Not Published).

Cerdan, M.G., et al., "Accurate Spatial and Temporal Transgene Expression Driven by a 3.8-Kilobase Promoter of the Bovine β-Casein Gene in the Lactating Mouse Mammary Gland," *Molecular Reproduction and Development* 49:236-245, Wiley-Liss (1998).

Alexander, L., et al., "Epidemiology of Acromegaly in the Newcastle Region," *Clin. Endocrinol.* 12:71-79, Blackwell Scientific Publications (1980).

Bartke, A., et al., "Neuroendocrine and Reproductive Consequences of Overexpression of Growth Hormone in Transgenic Mice," *Proc. Soc. Exp. Biol. Med.* 206:345-359, Blackwell Scientific Publications (1994).

Behncken, S.N., et al., "Aspartate 171 Is the Major Primate-specific Determinant of Human Growth Hormone," *J. Biol. Chem.* 272:27077-27083, The American Society for Biochemistry and Molecular Biology, Inc. (1997).

Bengtsson, B.-A., et al., "Epidemiology and Long-term Survival in Acromegaly," *Acta Med. Scand.* 223:327-335, The Almqvist & Wiksell Periodical Company (1988).

Bollano, E., et al., "Impairment of Cardiac Function and Bioenergetics in Adult Transgenic Mice Overexpressing the Bovine Growth Hormone Gene," *Endocrinol.* 141:2229-2235, The Endocrine Society (2000).

Brem, G., et al., "Production of transgenic mice, rabbits and pigs by microinjection into pronuclei," *Zuchthygiene* 20:251-252, Verlagsbuchhandlung (1985).

Brem, G., et al., "Multiple Consequences of Human Growth Hormone Expression in Transgenic Mice," *Mol. Biol. Med.* 6:531-547, Academic Press (1989).

Connell, J.M.C. and Davies, D.L., "Endocrine Hypertension: Thyroid Disease and Acromegaly," in: *Textbook of Hypertension*, Swales, J.D., ed., Blackwell Scientific Publications, pp. 959-968 (1994).

Costa, C., et al., "Transgenic rabbits overexpressing growth hormone develop acromegaly and diabetes mellitus," *FASEB J.* 12:1455-1460, The Federation of American Societies for Experimental Biology (1998).

Knoril, E. and Greep, R.O., "I. The Pituitary Hormones. The Physiology of Growth Hormone with Particular Reference to Its Action in the Rhesus Monkey and the "Species Specificity" Problem," in: *Recent Progress in Hormone Research*, Pincus, G., ed., Academic Press, pp. 1-69 (1959).

Lauteric, T.J., et al., "Reduced $^{125}$I-hGH Binding by Serum of Dwarf Pigs But Not By Serum of Dwarfed Poodles," *Comp. Biochem. Physiol.* 91A:15-19, Pergamon Press plc (1988).

Li, C.H., "Properties of and Structural Investigations on Growth Hormones Isolated from Bovine Monkey and Human Pituitary Glands," *Fed. Proc.* 16:775-783, Federation of American Societies for Experimental Biology (1957).

Martins, J.B., et al., "Cardiac Size and Function in Acromegaly," *Circulation* 56:863-869, American Heart Association, Inc. (1977).

Olsson, B., et al., "Bovine growth hormone-transgenic mice have major alterations in hepatic expression of metabolic genes," *Am. J. Physiol. Endocrinol. Metab.* 285:E504-E511, The American Physiological Society (first available May 2003).

Peterson, F.C. and Brooks, C.L., "The species specificity of growth hormone requires the cooperative interaction of two motifs," *FEBS Lett.* 472:276-282, Federation of European Biochemical Societies (2000).

Pursel, V.G., et al., "Genetic Engineering of Livestock," *Science* 244:1281-1288, American Association for the Advancement of Science (1989).

Pursel, V.G., et al., "Expression and performance in transgenic pigs," *J. Reprod. Fert. Suppl.* 40:235-245, Journals of Reproduction & Fertility Ltd. (1990).

Rexroad Jr., C.E., et al., "Insertion, expression and physiology of growth-regulating genes in ruminants," *J. Reprod. Fert., Suppl.* 41:119-124, Journals of Reproduction & Fertility Ltd. (1990).

Souza, S.C., et al., "A single arginine residue determines species specificity of the human growth hormone receptor," *Proc. Natl. Acad. Sci. USA* 92:959-963, National Academy of Science (1995).

Steger, R.W., et al., "Premature ageing in transgenic mice expressing different growth hormone genes," *J. Reprod. Fert., Suppl.* 46:61-75, Journals of Reproduction & Fertility Ltd. (1993).

Thorner, M.O., et al., "Chapter 9. The Anterior Pituitary," in: *Williams Textbook of Endocrinology*, 9$^{th}$ Ed., Wilson, J.D., eds., W.B. Saunders Company, pp. 249-307 (1998).

Valera, A., et al., "Glucose metabolism in transgenic mice containing a chimeric P-enolpyruvate carboxykinase/bovine growth hormone gene," *FASEB J.* 7:791-800, The Federation of American Societies for Experimental Biology (1993).

Wanke, R., et al., "Accelerated growth and visceral lesions in transgenic mice expressing foreign genes of the growth hormone family: an overview," *Pediatr. Nephrol.* 5:513-521, Springer International (1991).

Wanke, R., et al., "The GH-Transgenic Mouse as an Experimental Model for Growth Research: Clinical and Pathological Studies," *Horm. Res. 37*:74-87, S. Karger (1992).

Ward, K.A., et al., "The Insertion of Foreign DNA into Animal Cells," in: *Biotechnology for Livestock Production*, Animal Production and Health Division, FAO, Plenum Press, New York, NY, pp. 17-28 (1989).

Ward, K.A., et al., "The Direct Transfer of DNA by Embryo Microinjection," *Pro. 3rd. World Congr. Genetics Appl. Livestock Prod.*, Lincoln, NB, pp. 6-21 (1986).

Wolf, E., et al., "Effects of Long-Term Elevated Serum Levels of Growth Hormone on Life Expectancy of Mice: Lessons from Transgenic Animal Models," *Mech. Ageing and Develop. 68*:71-87, Elsevier Scientific Publishers Ireland Ltd. (1993).

Yi, S., et al., "Functional Promiscuity of Squirrel Monkey Growth Hormone Receptor Toward both Primate and Nonprimate Growth Hormones," *Mol. Biol. Evol. 19*:1083-1092, Oxford University Press (2002).

Brophy, B., et al., "Cloned transgenic cattle produce milk with higher levels of β-casein and κ-casein," *Nat. Biotechnol. 21*:157-162, Nature Publishing Group (Feb. 2003).

Oh, K.B., et al., "A hybrid bovine-β-casein/bGH gene directs transgene expression to the lung and mammary gland of transgenic mice," *Transgenic Res. 8*:307-311, Kluwer Academic Press (1999).

Office Action mailed Apr. 11, 2008 in Canadian Appl. No. 2,540,667, Arguelles et al., filed Sep. 29, 2004.

Office Action mailed Feb. 29, 2008 in Chinese Appl. No. 200480031507.8, Arguelles et al., filed Sep. 29, 2004.

Office Action mailed Oct. 9, 2007 in U.S. Appl. No. 10/952,376, Melo et al., filed Sep. 29, 2004.

Office Action mailed Jun. 27, 2008 in Russian Patent Application No. 2006114685, Melo et al., filed Sep. 29, 2004.

Derewenda, U., et al., "X-ray analysis of the single chain B29-A1 peptide-linked insulin molecule: A completely inactive analogue," *J Mol Biol 220*:425-433, Academic Press (1991).

Donnelly, M.I., et al., "Expression of a Highly Toxic Protein, Bax, in *Escherichia coli* by Attachment of a Leader Peptide Derived from the GroES Cochaperone," *Protein Expression and Purification 22*:422-429, Academic Press (2001).

Goossens, M., "hGH et biologie moléculaire," *Ann Endocrinol* (Paris) *47*:363-371, Elsevier Masson SAS (1986).

Hammer, R.E., et al., "Production of transgenic rabbits, sheep and pigs by microinjection," *Nature 315*:680-683, Nature Publishing Group (1985).

Kim, M.O., et al., "Transgene expression of biological active recombinant human granulocyte-colony stimulating factor (hG-CSF) into mouse urine," *Life Sciences 78*:1003-1009, Pergamon Press (2006).

Melo, E.O., et al., "Animal transgenesis: state of the art and applications," *J Appl Genet 48*:47-61, Institute of Plant Genetics, Polish Academy of Sciences (2007).

Niemann, H. and Kues, W.A., "Transgenic livestock: premises and promises," *Animal Reproduction Science 60-61*:277-293, Elsevier Science B.V. (2000).

Phelps, C.J. and Bartke, A., "Stimulatory Effect of Human, but not Bovine, Growth Hormone Expression on Numbers of Tuberoinfundibular Dopaminergic Neurons in Transgenic Mice," *Endocrinology 138*:2849-2855, The Endocrine Society (1997).

Salamone, D., et al., "High level expression of bioactive recombinant human growth hormone in the milk of a cloned transgenic cow," *J. Biotechnol. 124*:469-472, Elsevier Science Publishers (Jul. 2006).

Office Action mailed on Jul. 23, 2008 in U.S. Appl. No. 10/952,376, inventors Melo et al., filed Sep. 29, 2004.

Office Action mailed Dec. 1, 2008 in Canadian Patent Application No. 2,540,667, inventors Arguelles et al., filed Sep. 29, 2004.

U.S. Appl. No. 12/138,526, inventors Bercovich et al., filed Jun. 13, 2008 (Not Published).

U.S. Appl. No. 12/138,529, inventors Bercovich et al., filed Jun. 13, 2008 (Not Published).

Office Action mailed Jan. 14, 2009 in European Patent Application No. 04789169.2, inventors Arguelles et al., filed Sep. 29, 2004.

Lipinsky, D., et al., "Transgenic rabbit producing human growth hormone in milk," *J. Appl. Genet. 44*:165-174, Institute of Plant Genetics, Polish Academy of Sciences (2003).

ZhiXiang, W., "Adsorption chromatography and applied techniques of proteins," *Chin. J. of Pharm. 24*:520-522 (1993).

Unverified English Language Translation of ZhiXiang, W., "Adsorption chromatography and applied techniques of proteins," *Chin. J. of Pharm. 24*:520-522 (1993), Document NPL63.

\* cited by examiner

Figure 1A

Milk volume

Udder
- LA  Left anterior
- RA  Right anterior
- LP  Left posterior
- RP  Right posterior

| Date | Morning (ml) | | | | Morning total | Afternoon (ml) | | | | Afternoon total | Day total |
|---|---|---|---|---|---|---|---|---|---|---|---|
| | LA | RA | LP | RP | | LA | RA | LP | RP | | |
| 07/15/03 | 120 | 120 | 120 | 270 | 630 | 900 | -0 | -0 | -0 | 900 | 1530 |
| 07/16/03 | 140 | 120 | 220 | 320 | 800 | 90 | 70 | 200 | 200 | 560 | 1360 |
| 07/17/03 | 140 | 70 | 170 | 240 | 620 | 200 | 170 | 320 | 300 | 990 | 1610 |
| 07/18/03 | 220 | 120 | 240 | 370 | 950 | 220 | 150 | 320 | 270 | 960 | 1910 |
| 07/19/03 | 200 | 170 | 220 | 350 | 940 | 220 | 220 | 220 | 200 | 840 | 1780 |
| 07/20/03 | 220 | 170 | 400 | 350 | 1140 | 220 | 170 | 400 | 320 | 1110 | 2250 |
| 07/21/03 | 370 | 270 | 620 | 470 | 1730 | 270 | 220 | 475 | 370 | 1335 | 3065 |
| 07/22/03 | 270 | 125 | 500 | 400 | 1295 | 350 | 320 | 450 | 420 | 1540 | 2835 |
| 07/23/03 | 270 | 200 | 470 | 500 | 1440 | 280 | 320 | 560 | 570 | 1730 | 3170 |
| 07/24/03 | 300 | 220 | 470 | 370 | 1360 | 340 | 370 | 620 | 500 | 1830 | 3190 |
| 07/25/03 | 370 | 260 | 420 | 400 | 1450 | 340 | 440 | 510 | 560 | 1850 | 3300 |
| 07/26/03 | 350 | 400 | 500 | 550 | 1800 | 400 | 400 | 550 | 570 | 1920 | 3720 |
| 07/27/03 | 470 | 400 | 470 | 550 | 1890 | 420 | 420 | 520 | 550 | 1910 | 3800 |
| 07/28/03 | 300 | 370 | 350 | 450 | 1470 | 370 | 400 | 520 | 570 | 1860 | 3330 |
| 07/29/03 | 280 | 250 | 380 | 400 | 1310 | 320 | 330 | 500 | 520 | 1670 | 2980 |
| 07/30/03 | 270 | 300 | 420 | 450 | 1440 | 290 | 355 | 460 | 530 | 1635 | 3075 |
| 07/31/03 | 280 | 310 | 320 | 370 | 1280 | 345 | 440 | 550 | 550 | 1885 | 3165 |
| 08/01/03 | 300 | 400 | 400 | 420 | 1520 | 370 | 435 | 620 | 520 | 1945 | 3465 |
| 08/02/03 | 320 | 470 | 750 | 600 | 2140 | 320 | 320 | 550 | 450 | 1640 | 3780 |
| 08/03/03 | 350 | 420 | 400 | 450 | 1620 | 320 | 320 | 550 | 520 | 1710 | 3330 |
| 08/04/03 | 350 | 500 | 450 | 600 | 1900 | 320 | 420 | 500 | 420 | 1640 | 3540 |
| 08/05/03 | 280 | 380 | 400 | 550 | 1610 | 320 | 420 | 500 | 470 | 1810 | 3420 |
| 08/06/03 | 400 | 300 | 500 | 500 | 1700 | 420 | 370 | 660 | 540 | 1990 | 3690 |
| 08/07/03 | 540 | 520 | 520 | 520 | 2100 | 470 | 470 | 620 | 570 | 2130 | 4230 |
| 08/08/03 | 400 | 420 | 600 | 570 | 2010 | 450 | 520 | 700 | 650 | 2320 | 4330 |
| 08/09/03 | 520 | 520 | 420 | 520 | 1980 | 420 | 420 | 600 | 550 | 1990 | 3970 |
| 08/10/03 | 450 | 520 | 540 | 330 | 1840 | 300 | 300 | 500 | 550 | 1650 | 3490 |
| 08/11/03 | 520 | 520 | 820 | 720 | 2580 | 530 | 520 | 820 | 720 | 2590 | 5170 |
| 08/12/03 | 520 | 520 | 750 | 720 | 2510 | 380 | 490 | 680 | 680 | 2230 | 4740 |
| 08/13/03 | 470 | 480 | 700 | 770 | 2440 | 600 | 570 | 900 | 800 | 2870 | 5310 |
| 08/14/03 | 620 | 800 | 1200 | 1150 | 3770 | 1120 | | | | 1120 | 4890 |

| | Morning | Noon | Afternoon | | |
| --- | --- | --- | --- | --- | --- |
| 08/15/03 | 1950 | 1100 | 1100 | | 4150 |
| 08/16/03 | 1200 | 800 | 900 | | 2900 |
| 08/17/03 | 1500 | 1000 | 1000 | | 3500 |
| 08/18/03 | 1720 | 1000 | 1100 | | 3820 |
| 08/19/03 | 1800 | 1200 | 1100 | | 4100 |
| 08/20/03 | 1870 | 1200 | 1170 | | 4240 |
| 08/21/03 | 1670 | 1150 | 1160 | | 4180 |
| 08/22/03 | 2020 | 1300 | 1060 | | 4380 |
| 08/23/03 | 2000 | 1400 | 1150 | | 4550 |
| 08/24/03 | 2100 | 1200 | 1400 | | 4700 |
| 08/25/03 | 1800 | 700 | 870 | | 3370 |
| 08/26/03 | 1870 | 1170 | 1250 | | 4290 |
| 08/27/03 | 1700 | 1600 | 1700 | | 5000 |
| 08/28/03 | 2620 | 1300 | 1000 | | 4920 |

| Date | Morning | Noon | Afternoon | Day Total |
|---|---|---|---|---|
| 08/29/03 | 2550 | 1370 | 1750 | 5670 |
| 08/30/03 | 2350 | 1920 | 1900 | 6170 |
| 08/31/03 | 3020 | 1020 | 2350 | 6390 |
| 09/01/03 | 2400 | 1370 | 1350 | 5120 |
| 09/02/03 | 3000 | 1000 | 1650 | 5650 |
| 09/03/03 | 3020 | 1100 | 1600 | 5720 |
| 09/04/03 | 3120 | 1450 | 2000 | 6570 |
| 09/05/03 | 3020 | 1550 | 1750 | 6320 |
| 09/06/03 | 2720 | 1750 | 1700 | 6170 |
| 09/07/03 | 2700 | 2000 | 2000 | 6700 |
| 09/08/03 | 3300 | 1770 | 2070 | 7140 |
| 09/09/03 | 3520 | 2320 | 1720 | 7560 |
| 09/10/03 | 3620 | 1540 | 1740 | 6900 |
| 09/11/03 | 3470 | 1520 | 1770 | 6760 |
| 09/12/03 | 3720 | 1520 | 1720 | 6960 |
| 09/13/03 | 3570 | 1820 | 1820 | 7210 |
| 09/14/03 | 3120 | 2370 | 2020 | 7510 |
| 09/15/03 | 3820 | 1700 | 1700 | 7220 |
| 09/16/03 | 3570 | 1950 | 2000 | 7520 |
| 09/17/03 | 3870 | 1550 | 2100 | 7520 |
| 09/18/03 | 4020 | 1820 | 1950 | 7790 |
| 09/19/03 | 4020 | 1470 | 2300 | 7790 |
| 09/20/03 | 3720 | 1600 | 1950 | 7270 |
| 09/21/03 | 3420 | 2000 | 2100 | 7520 |
| 09/22/03 | 3950 | 1700 | 1600 | 7250 |
| 09/23/03 | 3500 | 1800 | 1900 | 7200 |
| 09/24/03 | 4100 | 1600 | 2200 | 7900 |
| 09/25/03 | 4000 | 1450 | 2200 | 7650 |
| 09/26/03 | 3800 | 1600 | 2100 | 7500 |
| 09/27/03 | 3500 | 1900 | 2100 | 7500 |
| 09/28/03 | 3750 | 2300 | 2200 | 8250 |
| 09/29/03 | 3500 | 1850 | 2600 | 7950 |
| 09/30/03 | | 1880 | 2250 | 4130 |
| 10/01/03 | 3300 | 2000 | 2350 | 7650 |
| 10/02/03 | 4200 | 2050 | 2200 | 8450 |
| 10/03/03 | 4000 | 2050 | 2500 | 8550 |
| 10/04/03 | 4000 | 2350 | 2300 | 8650 |
| 10/05/03 | 3500 | 2600 | 2500 | 8600 |
| 10/06/03 | 4300 | 2100 | 2600 | 9000 |
| 10/07/03 | 4350 | 2300 | 2300 | 9000 |
| 10/08/03 | 4500 | 2000 | 2700 | 9200 |
| 10/09/03 | 4650 | 2250 | 2500 | 9400 |
| 10/10/03 | 4100 | 2000 | 2700 | 8800 |
| 10/11/03 | 4500 | 2250 | 2500 | 9250 |
| 10/12/03 | 4350 | 2600 | 2000 | 9950 |
| 10/13/03 | 4500 | 2700 | 3000 | 9950 |
| 10/14/03 | 4100 | 2300 | 2750 | 9100 |
| 10/15/03 | 4600 | 3200 | 2300 | 10100 |
| 10/16/03 | 3950 | 2700 | 2700 | 9350 |
| 10/17/03 | 4000 | 2500 | 2150 | 8650 |
| 10/18/03 | 5100 | 2600 | 2100 | 9800 |
| 10/19/03 | 3900 | 2700 | 2500 | 9100 |
| 10/20/03 | 4700 | 1950 | 2500 | 9150 |
| 10/21/03 | 4200 | 2200 | 3800 | 10200 |
| 10/22/03 | 4100 | 2550 | 2400 | 9050 |
| 10/23/03 | 4450 | 2000 | 2300 | 8750 |

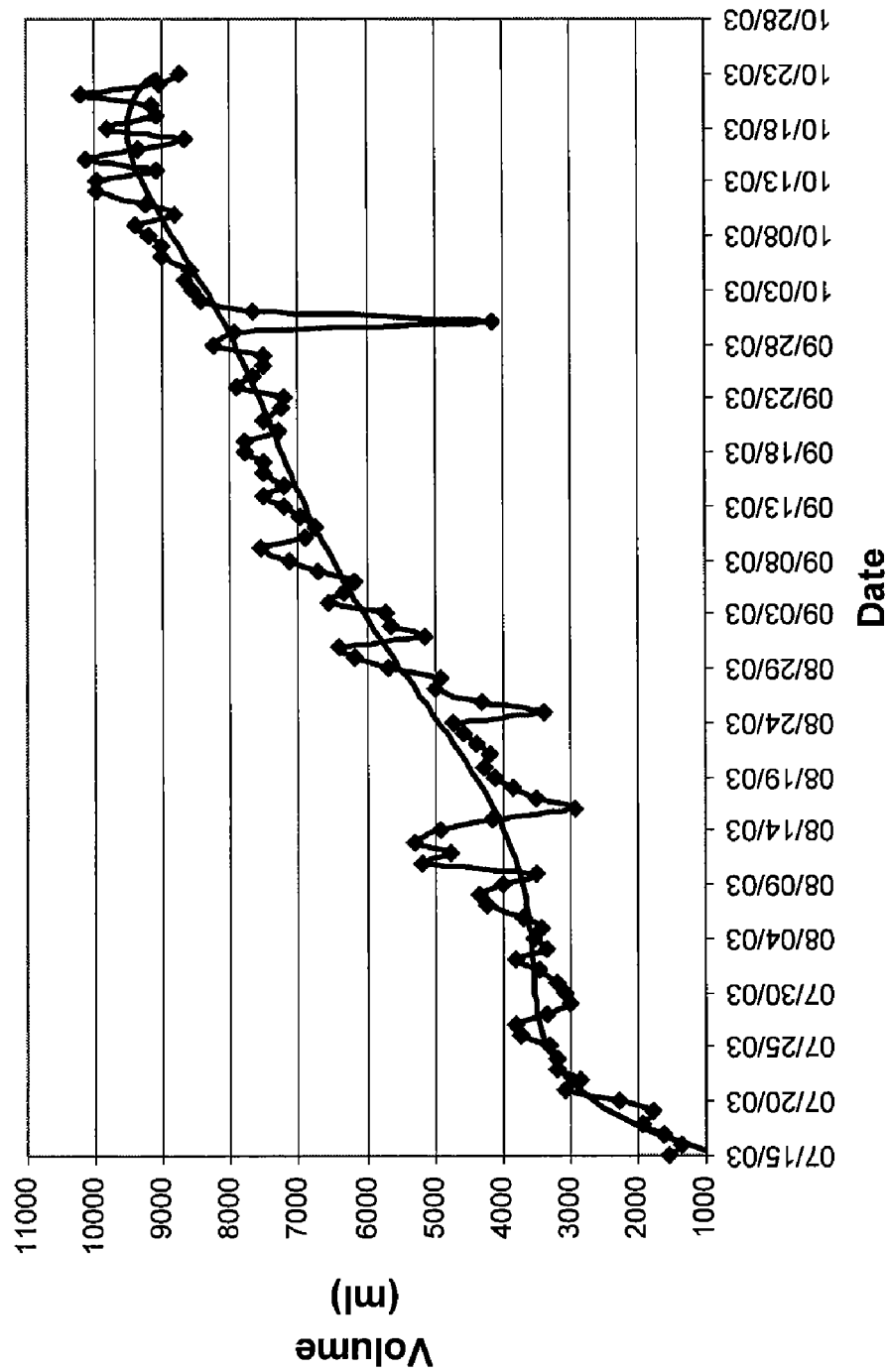

Figure 2A

Microbiology

Antibiotic treatment
Penicillin 5MU
Streptomycin 2gr
Dipyrone 1 gr

Udder
| | | | |
|---|---|---|---|
| LA | Left anterior | M | Morning |
| RA | Right anterior | N | Noon |
| LP | Left posterior | A | Afternoon |
| RP | Right posterior | | |

| Date | | LA | RA | LP | RP |
|---|---|---|---|---|---|
| 07/15/03 | | 4400 | 3000000 | 1500 | 44000 |
| 07/16/03 | M | 920 | 4000 | 1680 | 2640 |
| 07/16/03 | A | 1010 | 1070 | 13600 | 3700 |
| 07/17/03 | M | 960 | 4100 | 790000 | 1180 |
| 07/17/03 | A | 550 | 30000 | 10400 | 590 |
| 07/18/03 | M | 620 | 8800 | 108000 | 600 |
| 07/18/03 | A | 1440 | 1460 | 300 | 150 |
| 07/19/03 | M | 1330 | 30 | 200 | 2390 |
| 07/19/03 | A | 1430 | 5700 | 100 | 320 |
| 07/20/03 | M | 2850 | 70 | 600 | 1400 |
| 07/20/03 | A | 7600 | 360 | 400 | 320 |
| 07/21/03 | M | 8800 | 80 | 600 | 430 |
| 07/21/03 | A | 13700 | 200 | 440 | 150 |
| 07/22/03 | M | 8300 | 560 | 8700 | 1170 |
| 07/22/03 | A | 3500 | 1450 | 3900 | 850 |
| 07/23/03 | M | 1990 | 4200 | 730 | 1490 |
| 07/23/03 | A | 1070 | 410 | 730 | 1080 |
| 07/24/03 | M | 1000 | 1930 | NA | 950 |
| 07/24/03 | A | 320 | 1800 | 240 | 140 |
| 07/25/03 | M | 280 | 2230 | 70 | 170 |
| 07/25/03 | A | 710 | 110 | 150 | 40 |
| 07/26/03 | M | 4300 | 1160 | 160 | 250 |
| 07/26/03 | A | 1390 | 40 | 20 | 100 |
| 07/27/03 | M | 1240 | 4400 | 140 | 490 |
| 07/27/03 | A | 2350 | 40 | 350 | 250 |
| 07/28/03 | M | 7600 | 1340 | 1080 | 460 |
| 07/28/03 | A | 530 | 120 | 1500 | 200 |
| 07/29/03 | M | 5900 | 400 | 8300 | 300 |
| 07/29/03 | A | 1600 | 110 | 450 | 410 |
| 07/30/03 | M | 17800 | 950 | 370 | 880 |
| 07/30/03 | A | 1120 | 200 | 850 | 190 |
| 07/31/03 | M | 17500 | 1560 | 8500 | 4100 |
| 07/31/03 | A | 2520 | 580 | 250 | 190 |
| 08/01/03 | M | 17600 | 1840 | 330 | 1150 |
| 08/01/03 | A | 4400 | 4100 | 350 | 490 |
| 08/02/03 | M | 4300 | 430 | 530 | 830 |
| 08/02/03 | A | 1440 | 720 | 440 | 160 |
| 08/03/03 | M | 5700 | 4300 | 1080 | 780 |
| 08/03/03 | A | 7000 | 2030 | 750 | 1450 |
| 08/04/03 | M | 1710 | 890 | 420 | 3600 |
| 08/04/03 | A | 920 | 460 | 600 | 430 |
| 08/05/03 | M | 5100 | 2780 | 500 | 320 |
| 08/05/03 | A | 1540 | 440 | 660 | 640 |
| 08/06/03 | M | 5700 | 1720 | 420 | 1540 |
| 08/06/03 | A | 2140 | 750 | 840 | 340 |
| 08/07/03 | M | 1600 | 1720 | 70 | 130 |
| 08/07/03 | A | 560 | 710 | 140 | 90 |
| 08/08/03 | M | 1970 | 1346 | 20 | 40 |
| 08/08/03 | A | 380 | 510 | 210 | 10 |
| 08/09/03 | M | 1320 | 2010 | 2160 | 90 |
| 08/09/03 | A | 1810 | 5600 | 200 | 210 |
| 08/10/03 | M | 1160 | 2380 | 220 | 170 |
| 08/10/03 | A | 370 | 2770 | 30 | 100 |
| 08/11/03 | M | 1390 | 4000 | 90 | 40 |
| 08/11/03 | A | 1910 | 1590 | 330 | 140 |
| 08/12/03 | M | 5100 | 2820 | 1010 | 150 |
| 08/12/03 | A | 1550 | 5100 | 10 | 10 |
| 08/13/03 | M | 5000 | 7700 | 1600 | 160 |
| 08/13/03 | N | 700 | 2010 | 20 | 260 |
| 08/13/03 | A | 1430 | 4300 | 40 | 270 |
| 08/14/03 | M | 6500 | 2050 | 1430 | 590 |
| 08/14/03 | N | 820 | 1310 | 30 | 170 |

| | M | N | A |
|---|---|---|---|
| 08/14/03 | | | 630 |
| 08/15/03 | 550 | 290 | 1290 |
| 08/16/03 | 300 | 300 | 330 |
| 08/17/03 | 580 | 1070 | 580 |
| 08/18/03 | 1650 | 390 | 570 |
| 08/19/03 | 1210 | 500 | 530 |
| 08/20/03 | 20 | 530 | 1340 |
| 08/21/03 | 5700 | 480 | 860 |
| 08/22/03 | 30 | 1060 | 450 |
| 08/23/03 | 1860 | 440 | 290 |
| 08/24/03 | 410 | 950 | 11200 |
| 08/25/03 | 1780 | 920 | 560 |
| 08/26/03 | 620 | 800 | 1310 |
| 08/27/03 | 3800 | 1000 | 2530 |
| 08/28/03 | 6800 | 1930 | 840 |
| 08/29/03 | 1900 | 1460 | 1610 |
| 08/30/03 | 1270 | 990 | 810 |
| 08/31/03 | 980 | 1540 | 1860 |
| 09/01/03 | 390 | 2560 | 740 |
| 09/02/03 | 6400 | 1790 | 1710 |
| 09/03/03 | 210 | 1510 | 1290 |
| 09/04/03 | 3200 | 1470 | 930 |
| 09/05/03 | 1560 | 730 | 870 |
| 09/06/03 | 1820 | 1660 | 1200 |
| 09/07/03 | 4100 | 150 | 440 |
| 09/08/03 | 290 | 160 | 1100 |
| 09/09/03 | 5600 | 1370 | 1150 |
| 09/10/03 | 2290 | 1250 | 1050 |
| 09/11/03 | 1380 | 1610 | 1080 |
| 09/12/03 | 1950 | 30000 | 30000 |
| 09/13/03 | 1370 | 2440 | 2820 |
| 09/14/03 | 1320 | 1350 | 2150 |
| 09/15/03 | 1700 | 1200 | 1070 |
| 09/16/03 | 330 | 5900 | 14700 |
| 09/17/03 | 130 | 4300 | 1600 |
| 09/18/03 | 2730 | 1380 | 2320 |
| 09/19/03 | 3400 | 6100 | 6200 |
| 09/20/03 | 1700 | 10000 | 7600 |
| 09/21/03 | 10 | 10 | 120 |
| 09/22/03 | 10 | 30000 | 30 |
| 09/23/03 | 10 | 30 | 80 |
| 09/24/03 | 10 | 10 | 10 |
| 09/25/03 | 90 | 10 | 10 |
| 09/26/03 | 40 | 10 | 10 |
| 09/27/03 | 10 | 10 | 10 |
| 09/28/03 | 30 | 40 | 30 |
| 09/29/03 | 50 | 10 | 10 |
| 09/30/03 | | 10 | 30 |
| 10/01/03 | 30 | 10 | 20 |
| 10/02/03 | 160 | 190 | 170 |
| 10/03/03 | 10 | 160 | 60 |
| 10/04/03 | 10 | 250 | 230 |
| 10/05/03 | 290 | 410 | 120 |
| 10/06/03 | 300 | 150 | 310 |
| 10/07/03 | 830 | 950 | 480 |
| 10/08/03 | 170 | 960 | 720 |
| 10/09/03 | 870 | 590 | 330 |
| 10/10/03 | 100 | 590 | 230 |
| 10/11/03 | 500 | 360 | 220 |
| 10/12/03 | 90 | 1110 | 180 |
| 10/13/03 | 110 | 710 | 160 |
| 10/14/03 | 440 | 320 | 310 |
| 10/15/03 | 170 | 380 | 260 |
| 10/16/03 | 390 | 6800 | 60 |
| 10/17/03 | 560 | 6500 | 30000 |
| 10/18/03 | 2690 | 40 | 90 |
| 10/19/03 | 30000 | 30000 | 25500 |
| 10/20/03 | 150 | 25200 | 290 |
| 10/21/03 | 50 | 150 | 70 |
| 10/22/03 | 10 | 110 | 120 |
| 10/23/03 | 80 | 20 | 20 |

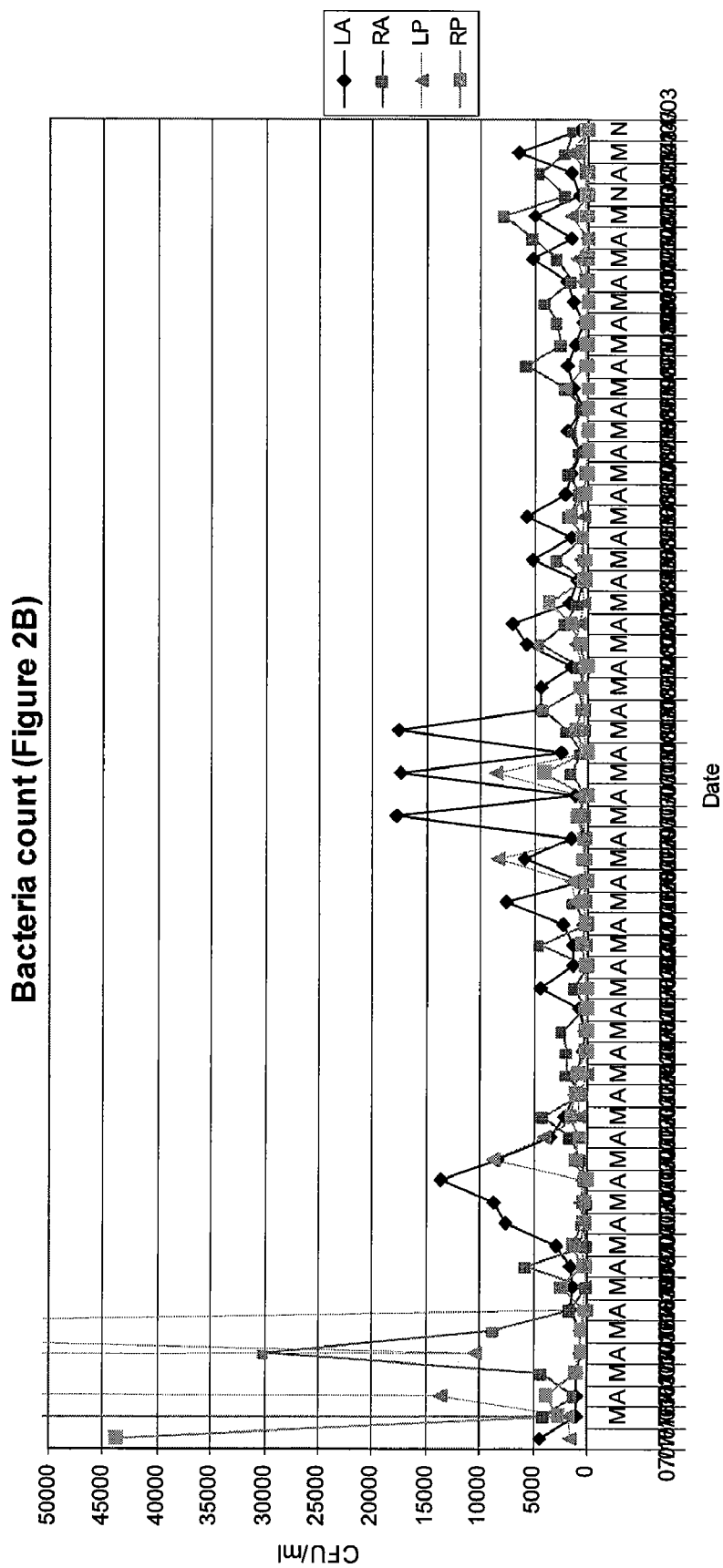

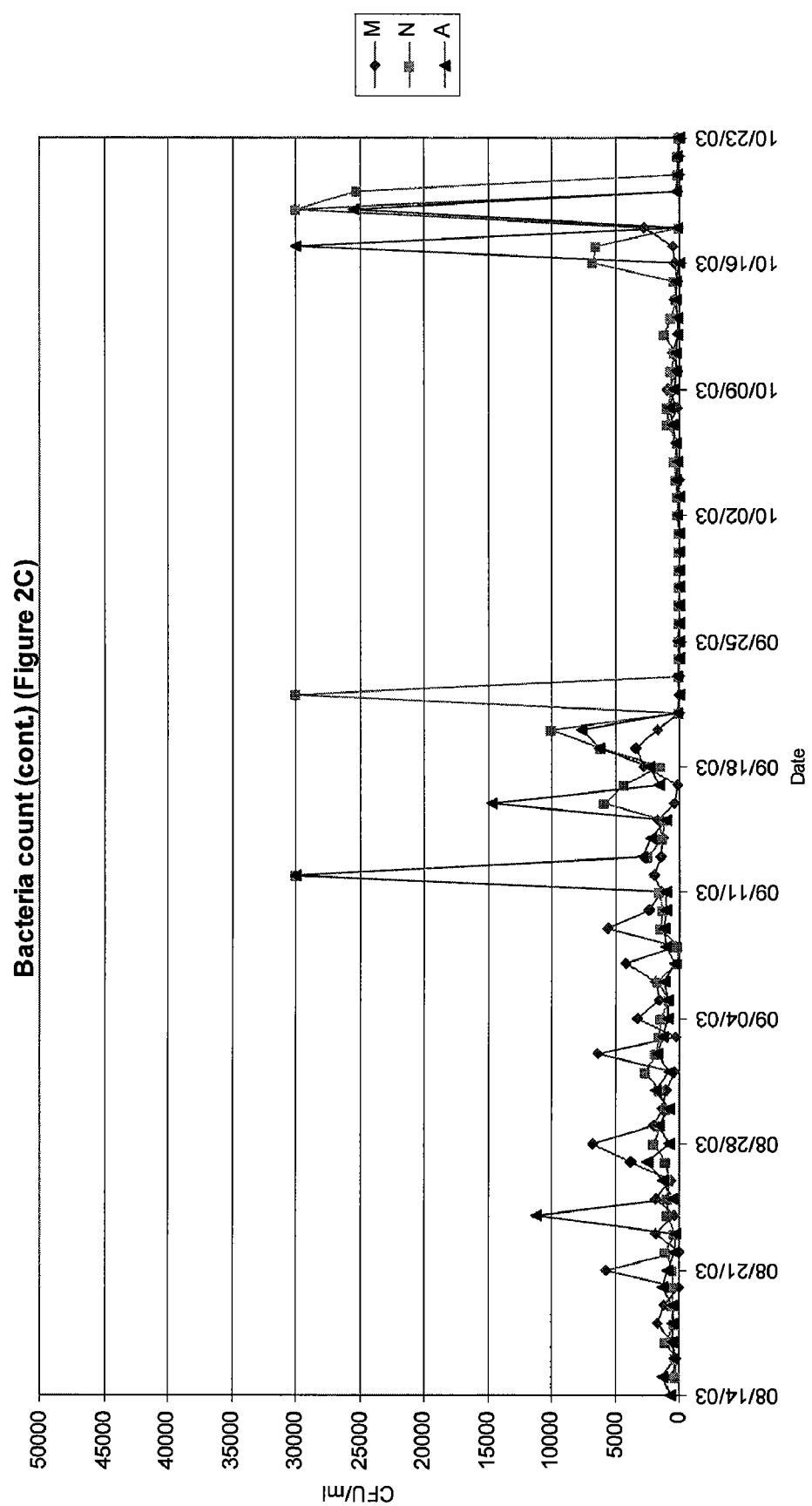

Figure 3A

Biological Activity

 MA  Morning Average
NA  Noon Average
AA  Afternoon Average
DA  Day Average

| Date | MA (UI/ml) | NA (UI/ml) | AA (UI/ml) | DA (UI/ml) | Date | MA (UI/ml) | NA (UI/ml) | AA (UI/ml) | DA (UI/ml) |
|---|---|---|---|---|---|---|---|---|---|
| 07/15/03 | 5.53 | | 5.53 | 5.53 | 09/20/03 | 19.10 | 15.10 | 18.10 | 17.43 |
| 07/16/03 | 13.62 | | 7.99 | 10.81 | 09/21/03 | 27.40 | 25.80 | 22.20 | 25.13 |
| 07/17/03 | 5.04 | | 11.83 | 8.44 | 09/22/03 | 21.00 | 23.90 | 26.30 | 23.73 |
| 07/18/03 | 8.05 | | 10.96 | 9.50 | 09/23/03 | 28.40 | 27.90 | 19.40 | 25.23 |
| 07/19/03 | | | 13.44 | 13.44 | 09/24/03 | 17.80 | 16.80 | 18.20 | 17.60 |
| 07/20/03 | | | 6.93 | 6.93 | 09/25/03 | 17.70 | 17.30 | 13.30 | 16.10 |
| 07/21/03 | 15.17 | | 9.19 | 12.18 | 09/26/03 | 16.60 | 14.50 | 15.70 | 15.60 |
| 07/22/03 | 11.89 | | 14.87 | 13.38 | 09/27/03 | 16.10 | 13.70 | 13.40 | 14.40 |
| 07/23/03 | 6.82 | | 12.77 | 9.80 | 09/28/03 | 15.00 | 15.40 | 17.40 | 15.93 |
| 07/24/03 | | | 15.73 | 15.73 | 09/29/03 | 15.80 | 15.20 | 15.20 | 15.40 |
| 07/25/03 | | | 24.65 | 24.65 | 09/30/03 | | 21.70 | 23.60 | 22.65 |
| 07/26/03 | | | 13.19 | 13.91 | 10/01/03 | 20.70 | 19.10 | 20.10 | 19.97 |
| 07/27/03 | | | 23.59 | 23.59 | 10/02/03 | 21.40 | 21.60 | 21.70 | 21.57 |
| 07/28/03 | | | 14.48 | 14.48 | 10/03/03 | 20.80 | 19.60 | 19.10 | 19.83 |
| 07/29/03 | | | 13.59 | 13.59 | 10/04/03 | 10.90 | 9.97 | 12.40 | 11.09 |
| 07/30/03 | | | 10.71 | 10.71 | 10/05/03 | 12.48 | 10.90 | 11.90 | 11.76 |
| 07/31/03 | | | 11.18 | 11.18 | 10/06/03 | 11.40 | 11.70 | 16.70 | 13.27 |
| 08/01/03 | | | 10.35 | 10.35 | 10/07/03 | 9.20 | 17.44 | 17.26 | 14.63 |
| 08/02/03 | | | 15.44 | 15.44 | 10/08/03 | 12.59 | 16.14 | 18.00 | 15.58 |
| 08/03/03 | | | 12.98 | 12.98 | 10/09/03 | 12.94 | 14.07 | 14.35 | 13.79 |
| 08/04/03 | | | 11.62 | 11.62 | 10/10/03 | 15.05 | 14.77 | 14.03 | 14.62 |
| 08/05/03 | | | 20.96 | 20.96 | 10/11/03 | 13.66 | 14.34 | 13.57 | 13.86 |
| 08/06/03 | | | 22.31 | 22.31 | 10/12/03 | 14.21 | 12.56 | 11.83 | 12.87 |
| 08/07/03 | | | 14.36 | 14.36 | 10/13/03 | 12.88 | 12.20 | 12.11 | 12.40 |
| 08/08/03 | | | 12.63 | 12.63 | 10/14/03 | 14.55 | 14.76 | 13.62 | 14.31 |
| 08/09/03 | | | 12.05 | 12.05 | 10/15/03 | 13.70 | 10.07 | 15.23 | 13.00 |
| 08/10/03 | | | 14.69 | 14.69 | 10/16/03 | 15.45 | 13.22 | 14.36 | 14.34 |
| 08/11/03 | 17.40 | | 18.20 | 17.80 | 10/17/03 | 15.48 | 12.60 | | 14.04 |
| 08/12/03 | 17.10 | | 17.50 | 17.30 | 10/18/03 | 12.49 | 10.50 | 13.12 | 12.04 |
| 08/13/03 | 16.60 | | 15.70 | 16.15 | 10/19/03 | 25.00 | 14.40 | 13.80 | 17.73 |
| 08/14/03 | 15.60 | | 15.60 | 15.60 | 10/20/03 | 13.80 | 14.20 | 14.70 | 14.23 |
| 08/15/03 | | 11.50 | 14.20 | 12.85 | 10/21/03 | 14.20 | 13.40 | 12.90 | 13.50 |
| 08/16/03 | | 12.00 | 11.50 | 11.75 | 10/22/03 | 15.00 | 14.00 | 38.00 | 22.33 |
| 08/17/03 | 10.10 | 9.60 | 12.50 | 10.73 | 10/23/03 | 23.50 | 22.40 | | 22.95 |
| 08/18/03 | 9.50 | 9.70 | 9.20 | 9.47 | Average | 16.56 | 15.96 | 17.02 | 15.69 |
| 08/19/03 | 13.40 | 14.30 | 12.30 | 13.33 | | | | | |
| 08/20/03 | 10.80 | 10.90 | 12.00 | 11.23 | | | | | |
| 08/21/03 | 12.70 | 10.20 | 11.10 | 11.33 | | | | | |
| 08/22/03 | 13.60 | 12.20 | 11.80 | 12.53 | | | | | |
| 08/23/03 | 12.30 | 11.60 | 10.50 | 11.47 | | | | | |
| 08/24/03 | 10.00 | 10.30 | 9.20 | 9.83 | | | | | |
| 08/25/03 | 17.90 | 16.10 | 17.00 | 17.00 | | | | | |
| 08/26/03 | 17.80 | 16.00 | 15.70 | 16.50 | | | | | |
| 08/27/03 | 15.80 | 16.10 | 15.20 | 15.70 | | | | | |
| 08/28/03 | 16.80 | 16.60 | 16.10 | 16.50 | | | | | |
| 08/29/03 | 16.60 | 16.40 | 19.30 | 17.43 | | | | | |
| 08/30/03 | 9.70 | 10.50 | 11.20 | 10.47 | | | | | |
| 08/31/03 | 11.40 | 12.40 | 10.30 | 11.37 | | | | | |
| 09/01/03 | 9.50 | 10.20 | 11.80 | 10.50 | | | | | |
| 09/02/03 | 20.50 | 22.10 | 23.20 | 21.93 | | | | | |
| 09/03/03 | 19.70 | 23.00 | 22.70 | 21.80 | | | | | |
| 09/04/03 | 25.40 | 25.60 | 31.70 | 27.57 | | | | | |
| 09/05/03 | 24.90 | 21.40 | 31.30 | 25.87 | | | | | |
| 09/06/03 | 15.80 | 16.40 | 14.30 | 15.50 | | | | | |
| 09/07/03 | 13.20 | 14.60 | 13.00 | 13.60 | | | | | |
| 09/08/03 | 15.30 | 10.50 | 11.30 | 12.37 | | | | | |
| 09/09/03 | 13.30 | 16.40 | 17.50 | 15.73 | | | | | |
| 09/10/03 | 9.00 | 11.70 | 13.43 | 11.38 | | | | | |
| 09/11/03 | 28.80 | 10.47 | 11.03 | 16.77 | | | | | |
| 09/12/03 | 13.20 | 11.33 | 13.20 | 12.58 | | | | | |
| 09/13/03 | 9.68 | 9.60 | 10.35 | 9.88 | | | | | |
| 09/14/03 | 14.90 | 14.40 | 11.20 | 13.50 | | | | | |
| 09/15/03 | 13.40 | 14.30 | 16.20 | 14.63 | | | | | |
| 09/16/03 | 16.90 | 15.60 | 14.30 | 15.60 | | | | | |
| 09/17/03 | 16.50 | 17.80 | 17.60 | 17.30 | | | | | |
| 09/18/03 | | | 18.50 | 18.50 | | | | | |
| 09/19/03 | | | 20.90 | 20.90 | | | | | |

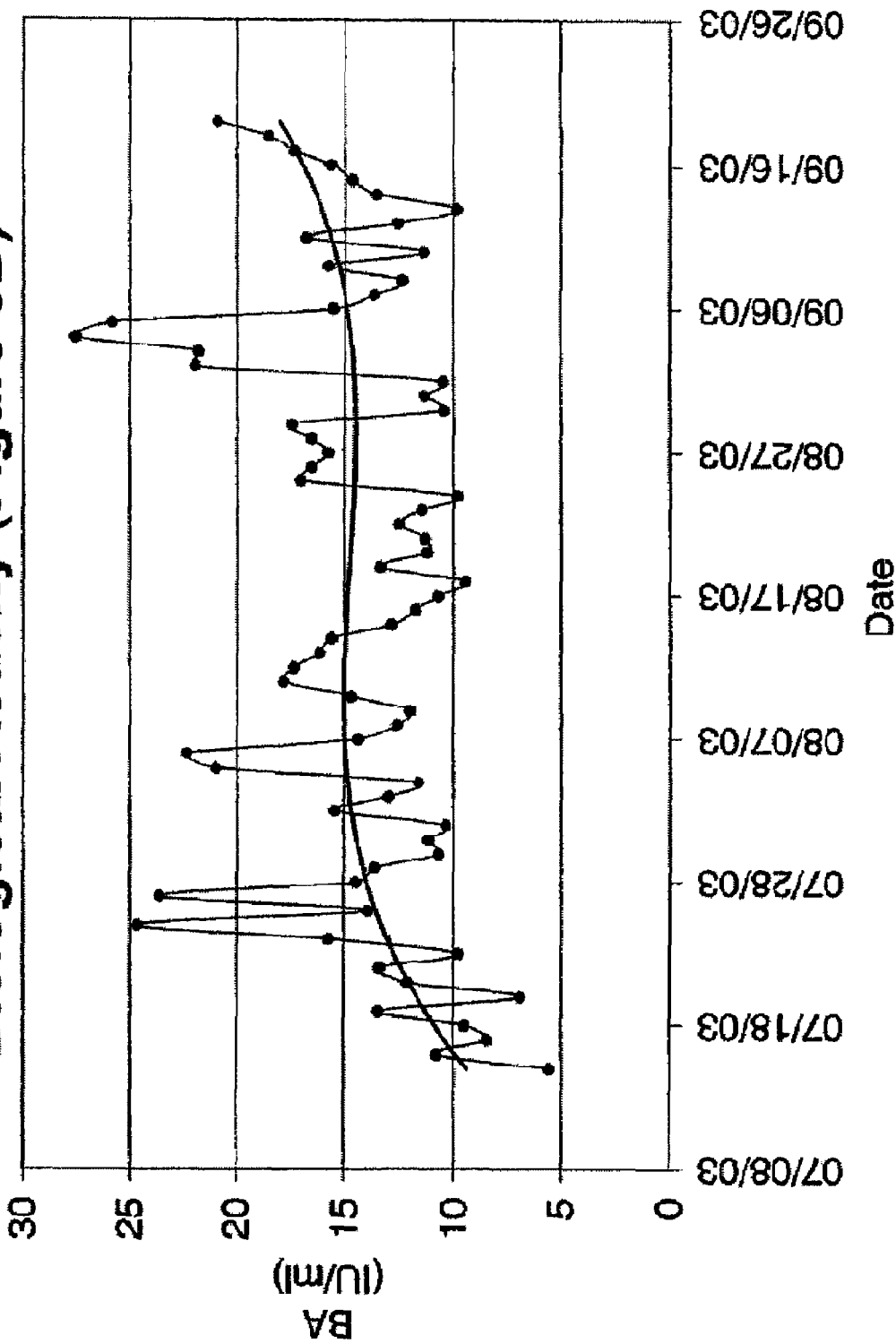

Figure 4A

MASS: calculated as BA/SAxV (mg=IU/ml/IU/mg) x ml)
Where BA: biological activity (IU/ml), SA: specific activity (3 IU/mg), V: volume (ml)

| Date | Mass Day Total (mg) | Date | Mass Day Total (mg) |
|---|---|---|---|
| 07/15/03 | 2821 | 09/16/03 | 39104 |
| 07/16/03 | 4899 | 09/17/03 | 43365 |
| 07/17/03 | 4527 | 09/18/03 | 45000 |
| 07/18/03 | 6050 | 09/19/03 | 54270 |
| 07/19/03 | 7977 | 09/20/03 | 42247 |
| 07/20/03 | 5196 | 09/21/03 | 63001 |
| 07/21/03 | 12443 | 09/22/03 | 57356 |
| 07/22/03 | 12645 | 09/23/03 | 60560 |
| 07/23/03 | 10353 | 09/24/03 | 46347 |
| 07/24/03 | 16726 | 09/25/03 | 41055 |
| 07/25/03 | 17000 | 09/26/03 | 39000 |
| 07/26/03 | 17248 | 09/27/03 | 36000 |
| 07/27/03 | 16500 | 09/28/03 | 43817 |
| 07/28/03 | 16073 | 09/29/03 | 40810 |
| 07/29/03 | 13500 | 09/30/03 | 31182 |
| 07/30/03 | 10978 | 10/01/03 | 50915 |
| 07/31/03 | 11792 | 10/02/03 | 60746 |
| 08/01/03 | 11957 | 10/03/03 | 56525 |
| 08/02/03 | 19454 | 10/04/03 | 31976 |
| 08/03/03 | 14408 | 10/05/03 | 33712 |
| 08/04/03 | 13711 | 10/06/03 | 39800 |
| 08/05/03 | 15000 | 10/07/03 | 43900 |
| 08/06/03 | 15000 | 10/08/03 | 47768 |
| 08/07/03 | 20248 | 10/09/03 | 43198 |
| 08/08/03 | 18229 | 10/10/03 | 42876 |
| 08/09/03 | 15946 | 10/11/03 | 42725 |
| 08/10/03 | 17089 | 10/12/03 | 42674 |
| 08/11/03 | 30675 | 10/13/03 | 41116 |
| 08/12/03 | 27334 | 10/14/03 | 43407 |
| 08/13/03 | 28586 | 10/15/03 | 43767 |
| 08/14/03 | 25428 | 10/16/03 | 44703 |
| 08/15/03 | 17776 | 10/17/03 | 40482 |
| 08/16/03 | 11358 | 10/18/03 | 39320 |
| 08/17/03 | 12522 | 10/19/03 | 53791 |
| 08/18/03 | 12054 | 10/20/03 | 43412 |
| 08/19/03 | 18222 | 10/21/03 | 45900 |
| 08/20/03 | 15876 | 10/22/03 | 67372 |
| 08/21/03 | 15791 | 10/23/03 | 66938 |
| 08/22/03 | 18299 | | |
| 08/23/03 | 17391 | | |
| 08/24/03 | 15406 | | |
| 08/25/03 | 19097 | | |
| 08/26/03 | 23595 | | |
| 08/27/03 | 26167 | | |
| 08/28/03 | 27060 | | |
| 08/29/03 | 23949 | | |
| 08/30/03 | 21526 | | |
| 08/31/03 | 24211 | | |
| 09/01/03 | 17920 | | |
| 09/02/03 | 41308 | | |
| 09/03/03 | 41565 | | |
| 09/04/03 | 60371 | | |
| 09/05/03 | 54492 | | |
| 09/06/03 | 31878 | | |
| 09/07/03 | 30373 | | |
| 09/08/03 | 29433 | | |
| 09/09/03 | 39648 | | |
| 09/10/03 | 26166 | | |
| 09/11/03 | 37781 | | |
| 09/12/03 | 29178 | | |
| 09/13/03 | 23737 | | |
| 09/14/03 | 33795 | | |
| 09/15/03 | 35218 | | |

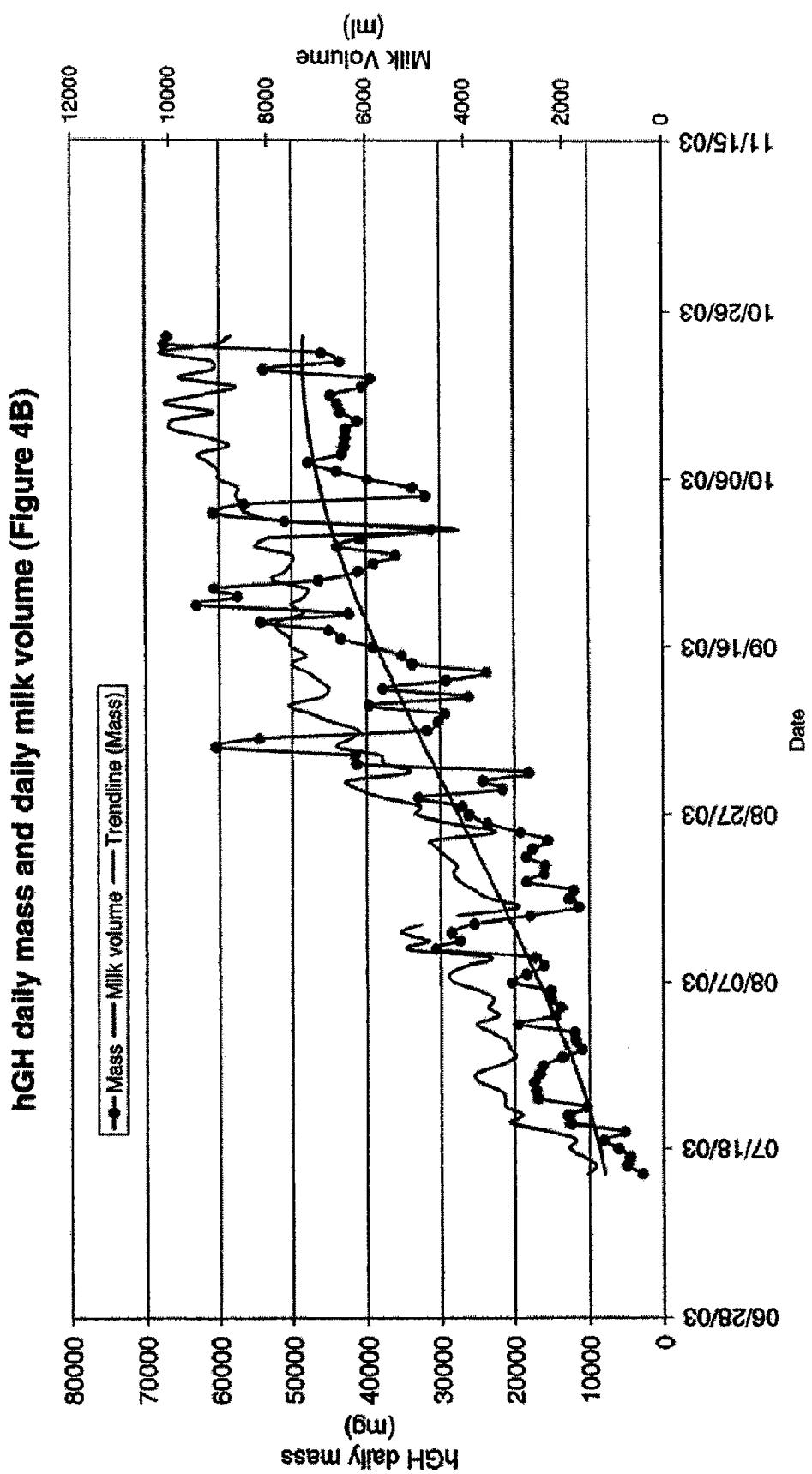

Figure 5A

| Date | [hGH] in Serum | Date | [hGH] in Serum | Date | hGH mass in Milk | Date | hGH mass in Milk | Date | [IGF-1] in Serum | Date | [IGF-1] in Serum |
|---|---|---|---|---|---|---|---|---|---|---|---|
| 09/24/02 | 0.05 | 10/10/03 | 633.00 | 07/15/03 | 2799 | 09/03/03 | 41565 | 04/01/03 | 230.00 | 06/25/04 | 534.00 |
| 12/04/02 | 0.05 | 10/10/03 | 644.00 | 07/16/03 | 5264 | 09/04/03 | 60371 | 04/15/03 | 290.00 | 07/07/04 | 494.00 |
| 12/10/02 | 0.11 | 10/16/03 | 685.00 | 07/17/03 | 4951 | 09/05/03 | 54492 | 04/22/03 | 330.00 | 07/28/04 | 568.00 |
| 12/15/02 | 0.07 | 10/21/03 | 2469.00 | 07/18/03 | 5917 | 09/06/03 | 31878 | 04/25/03 | 110.00 | 08/03/04 | 646.00 |
| 12/17/02 | 0.05 | 11/04/03 | 593.00 | 07/19/03 | 7977 | 09/07/03 | 30373 | 04/29/03 | 170.00 | 08/10/04 | 500.00 |
| 12/26/02 | 0.08 | 11/18/03 | 2375.00 | 07/20/03 | 5196 | 09/08/03 | 29433 | 05/06/03 | 446.00 | 08/13/04 | 380.00 |
| 01/08/03 | 0.05 | 12/02/03 | 1120.00 | 07/21/03 | 12443 | 09/09/03 | 39648 | 05/13/03 | 657.00 | | |
| 01/14/03 | 0.05 | 12/16/03 | 741.00 | 07/22/03 | 13263 | 09/10/03 | 26166 | 05/27/03 | 530.00 | | |
| 01/21/03 | 0.05 | 12/18/03 | 834.00 | 07/23/03 | 10619 | 09/11/03 | 37781 | 06/10/03 | 376.00 | | |
| 01/28/03 | 0.05 | 12/19/03 | 1584.00 | 07/24/03 | 16726 | 09/12/03 | 29178 | 06/17/03 | 269.00 | | |
| 02/04/03 | 0.05 | 12/20/03 | 1543.00 | 07/25/03 | 17000 | 09/13/03 | 23737 | 06/24/03 | 305.00 | | |
| 02/11/03 | 0.09 | 12/22/03 | 1630.00 | 07/26/03 | 17248 | 09/14/03 | 33795 | 07/01/03 | 424.00 | | |
| 02/18/03 | 0.05 | 12/24/03 | 1110.00 | 07/27/03 | 16500 | 09/15/03 | 35218 | 07/08/03 | 234.00 | | |
| 02/25/03 | 0.16 | 12/27/03 | 1071.00 | 07/28/03 | 16073 | 09/16/03 | 39104 | 07/15/03 | 375.00 | | |
| 03/04/03 | 1.10 | 12/30/03 | 1877.00 | 07/29/03 | 13500 | 09/17/03 | 43365 | 07/22/03 | 256.00 | | |
| 03/12/03 | 1.20 | 01/05/04 | 893.00 | 07/30/03 | 10978 | 09/18/03 | 45000 | 08/05/03 | 591.00 | | |
| 03/20/03 | 2.60 | 01/07/04 | 462.00 | 07/31/03 | 11792 | 09/19/03 | 54270 | 08/15/03 | 265.00 | | |
| 03/25/03 | 2.10 | 01/09/04 | 480.00 | 08/01/03 | 11957 | 09/20/03 | 42247 | 08/26/03 | 325.00 | | |
| 04/01/03 | 3.40 | 01/14/04 | 982.00 | 08/02/03 | 19454 | 09/21/03 | 63001 | 09/02/03 | 488.00 | | |
| 04/08/03 | 11.10 | 01/16/04 | 562.00 | 08/03/03 | 14408 | 09/22/03 | 57356 | 09/09/03 | 998.00 | | |
| 04/15/03 | 14.80 | 02/02/04 | 2616.00 | 08/04/03 | 13711 | 09/23/03 | 60560 | 09/16/03 | 726.00 | | |
| 04/22/03 | 138.00 | 02/05/04 | 2335.00 | 08/05/03 | 15000 | 09/24/03 | 46347 | 09/23/03 | 714.00 | | |
| 04/22/03 | 129.00 | 02/10/04 | 993.00 | 08/06/03 | 15000 | 09/25/03 | 41055 | 09/30/03 | 724 | | |
| 04/22/03 | 116.00 | 02/17/04 | 621.00 | 08/07/03 | 20248 | 09/26/03 | 39000 | 10/10/03 | 990.00 | | |
| 04/22/03 | 109.00 | 03/10/04 | 1063.00 | 08/08/03 | 18229 | 09/27/03 | 36000 | 10/16/03 | 1035.00 | | |
| 04/22/03 | 94.20 | 03/24/04 | 767.00 | 08/09/03 | 15946 | 09/28/03 | 43817 | 10/21/03 | 685.00 | | |
| 04/22/03 | 116.00 | 04/16/04 | 924.00 | 08/10/03 | 17089 | 09/29/03 | 40810 | 11/04/03 | 502.00 | | |
| 04/22/03 | 97.10 | 05/19/04 | 1566.00 | 08/11/03 | 30675 | 09/30/03 | 31182 | 11/18/03 | 530.00 | | |
| 04/22/03 | 118.00 | 06/01/04 | 1313.00 | 08/12/03 | 27334 | 10/01/03 | 50915 | 12/02/03 | 814.00 | | |
| 04/22/03 | 125.00 | 06/15/04 | 978.00 | 08/13/03 | 28586 | 10/02/03 | 50746 | 12/16/03 | 1154.00 | | |
| 04/22/03 | 107.00 | 06/25/04 | 1369.00 | 08/14/03 | 25428 | 10/03/03 | 56525 | 12/18/03 | 522.00 | | |
| 04/29/03 | 113.00 | 07/07/04 | 900.00 | 08/15/03 | 17776 | 10/04/03 | 31976 | 12/19/03 | 712.00 | | |
| 05/06/03 | 75.30 | 07/28/04 | 760.00 | 08/16/03 | 11358 | 10/05/03 | 33712 | 12/20/03 | 350.00 | | |
| 05/13/03 | 213.00 | 08/03/04 | 903.00 | 08/17/03 | 12522 | 10/06/03 | 39800 | 12/22/03 | 382.00 | | |
| 05/21/03 | 127.00 | 08/10/04 | 548.00 | 08/18/03 | 12054 | 10/07/03 | 43900 | 12/24/03 | 290.00 | | |
| 05/27/03 | 206.00 | 08/13/04 | 396.00 | 08/19/03 | 18222 | 10/08/03 | 47768 | 12/27/03 | 496.00 | | |
| 06/10/03 | 300.00 | 08/20/04 | 652.00 | 08/20/03 | 15876 | 10/09/03 | 43198 | 12/30/03 | 730.00 | | |
| 06/17/03 | 1350.00 | 08/31/04 | 1185.00 | 08/21/03 | 15791 | 10/10/03 | 42876 | 01/07/04 | 380.00 | | |
| 06/24/03 | 1521.00 | | | 08/22/03 | 18299 | 10/11/03 | 42725 | 01/14/04 | 370.00 | | |
| 07/01/03 | 727.00 | | | 08/23/03 | 17391 | 10/12/03 | 42674 | 01/20/04 | 686.00 | | |
| 07/08/03 | 669.00 | | | 08/24/03 | 15406 | 10/13/03 | 41116 | 02/02/04 | 654.00 | | |
| 07/15/03 | 3652.00 | | | 08/25/03 | 19097 | 10/14/03 | 43407 | 02/10/04 | 289.00 | | |
| 07/22/03 | 255.00 | | | 08/26/03 | 23595 | 10/15/03 | 43767 | 02/17/04 | 77.00 | | |
| 08/05/03 | 419.00 | | | 08/27/03 | 26167 | 10/16/03 | 44703 | 03/10/04 | 179.00 | | |
| 08/15/03 | 775.00 | | | 08/28/03 | 27060 | 10/17/03 | 40482 | 03/24/04 | 282.00 | | |
| 08/26/03 | 197.00 | | | 08/29/03 | 32949 | 10/18/03 | 39320 | | 431.00 | | |
| 09/02/03 | 704.00 | | | 08/30/03 | 21526 | 10/19/03 | 53791 | | 597.00 | | |
| 09/09/03 | 711.00 | | | 08/31/03 | 24211 | 10/20/03 | 43412 | 04/16/04 | 402.00 | | |
| 09/23/03 | 682.00 | | | 09/01/03 | 17920 | 10/21/03 | 45900 | 05/19/04 | 347.00 | | |
| 09/23/03 | 1420.00 | | | 09/02/03 | 41308 | 10/22/03 | 67372 | 06/01/04 | 347.00 | | |
| 09/30/03 | 991.00 | | | | | 10/23/03 | 66938 | 06/15/04 | 401.00 | | |

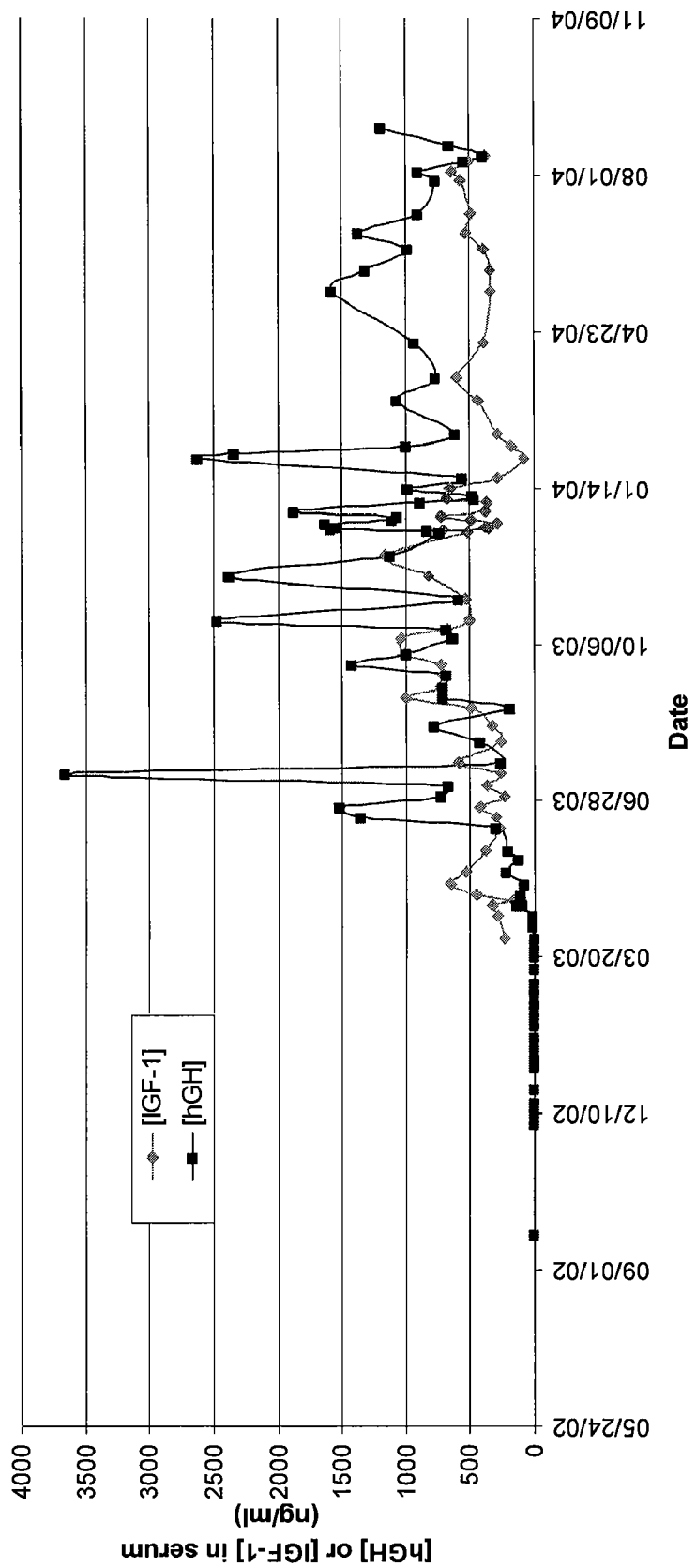

Figure 6A (Subclone #1)

| Date | [IGF-1] in Serum | Date | [hGH] in Serum |
|---|---|---|---|
| 01/05/04 | 90.00 | 01/05/04 | 0.50 |
| 01/06/04 | 74.00 | 01/06/04 | 0.05 |
| 01/07/04 | 93.00 | 01/07/04 | 0.05 |
| 01/08/04 | 107.00 | 01/08/04 | 0.05 |
| 01/12/04 | 99.00 | 01/12/04 | 0.05 |
| 01/26/04 | 46.00 | 01/20/04 | 0.05 |
| 02/02/04 | 30.00 | 02/05/04 | 0.05 |
| 02/10/04 | 83.00 | 02/17/04 | 0.05 |
| 02/17/04 | 43.00 | 03/02/04 | 0.05 |
| 03/10/04 | 46.00 | 03/24/04 | 0.05 |
| 03/24/04 | 18.00 | 04/16/04 | 0.05 |
| 04/16/04 | 50.00 | 04/23/04 | 0.07 |
| 04/23/04 | 78.00 | 05/19/04 | 0.05 |
| 05/19/04 | 77.00 | 06/01/04 | 0.07 |
| 06/01/04 | 92.00 | 06/15/04 | 0.33 |
| 06/15/04 | 99.00 | 06/25/04 | 1.00 |
| 06/25/04 | 50.00 | 07/07/04 | 3.40 |
| 07/07/04 | 27.00 | 07/28/04 | 3.00 |
| 07/28/04 | 80.00 | 08/03/04 | 2.50 |
| 08/03/04 | 57.00 | 08/10/04 | 3.60 |
| 08/10/04 | 85.00 | 08/31/04 | 18.10 |

Figure 6B (Subclone #2)

| Date | [IGF-1] in Serum | Date | [hGH] in Serum |
|---|---|---|---|
| 01/12/04 | 123.00 | 01/12/04 | 0.05 |
| 01/15/04 | 46.00 | 01/15/04 | 0.05 |
| 01/16/04 | 22.00 | 01/16/04 | 1.40 |
| 01/17/04 | 27.00 | 01/17/04 | 0.05 |
| 01/20/04 | 34.00 | 01/20/04 | 0.18 |
| 01/26/04 | 37.00 | 01/26/04 | 0.05 |
| 02/02/04 | 26.00 | 02/02/04 | 1.50 |
| 02/10/04 | 11.00 | 02/05/04 | 0.05 |
| 02/17/04 | 38.00 | 02/17/04 | 0.05 |
| 03/10/04 | 27.00 | 03/02/04 | 0.05 |
| 03/24/04 | 23.00 | 03/10/04 | 0.21 |
| 04/16/04 | 17.00 | 03/24/04 | 0.05 |
| 04/23/04 | 28.00 | 04/16/04 | 0.05 |
| 05/19/04 | 31.00 | 04/23/04 | 0.05 |
| 06/01/04 | 33.00 | 05/19/04 | 0.05 |
| 06/15/04 | 42.00 | 06/01/04 | 0.05 |
| 06/25/04 | 25.00 | 06/15/04 | 0.05 |
| 07/07/04 | 15.00 | 06/25/04 | 0.05 |
| 07/28/04 | 52.00 | 07/07/04 | 0.08 |
| 08/03/04 | 67.00 | 07/28/04 | 0.76 |
| 08/10/04 | 85.00 | 08/03/04 | 0.52 |
|  |  | 08/10/04 | 0.98 |
|  |  | 08/20/04 | 1.50 |
|  |  | 08/31/04 | 2.80 |

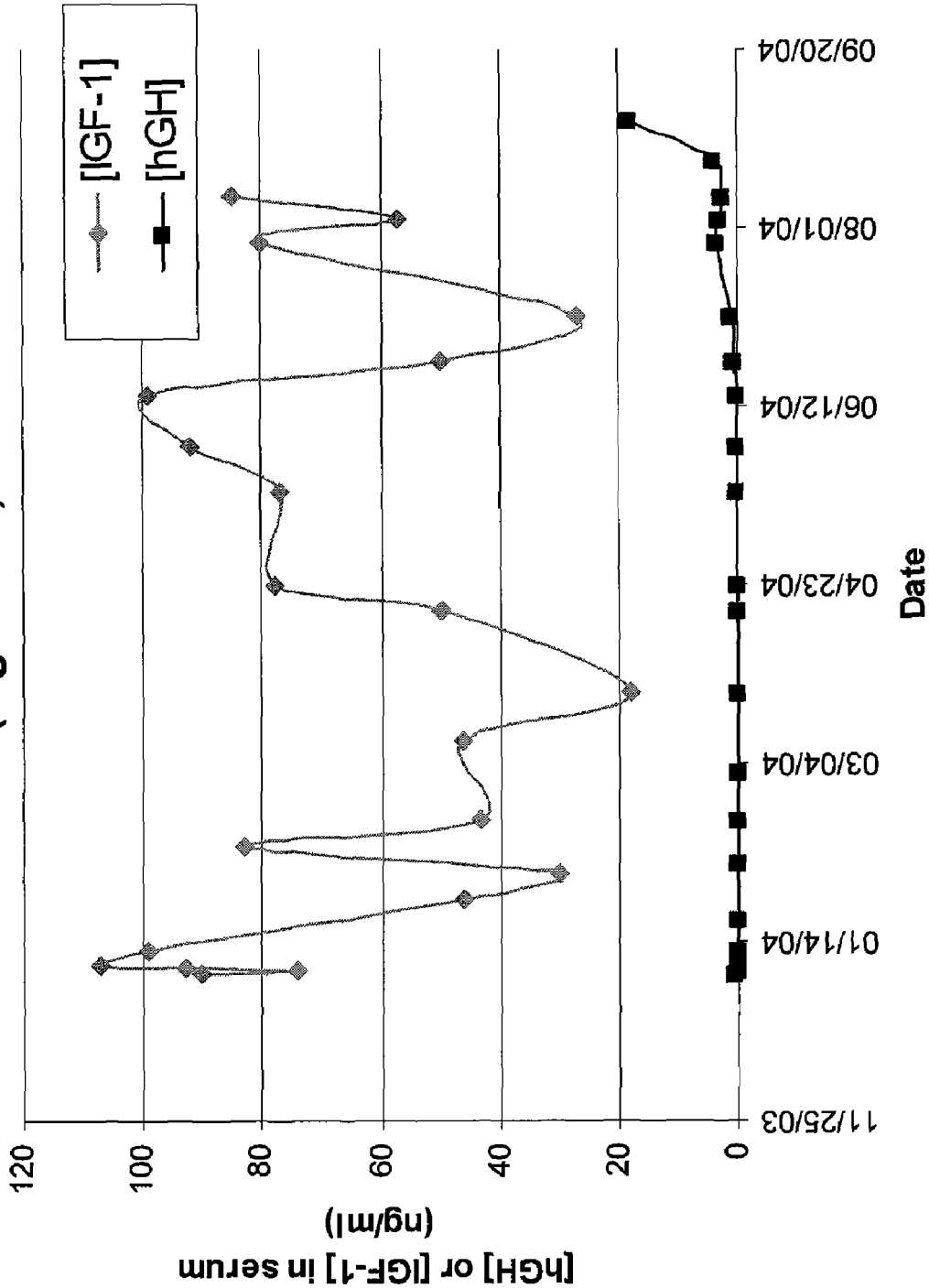

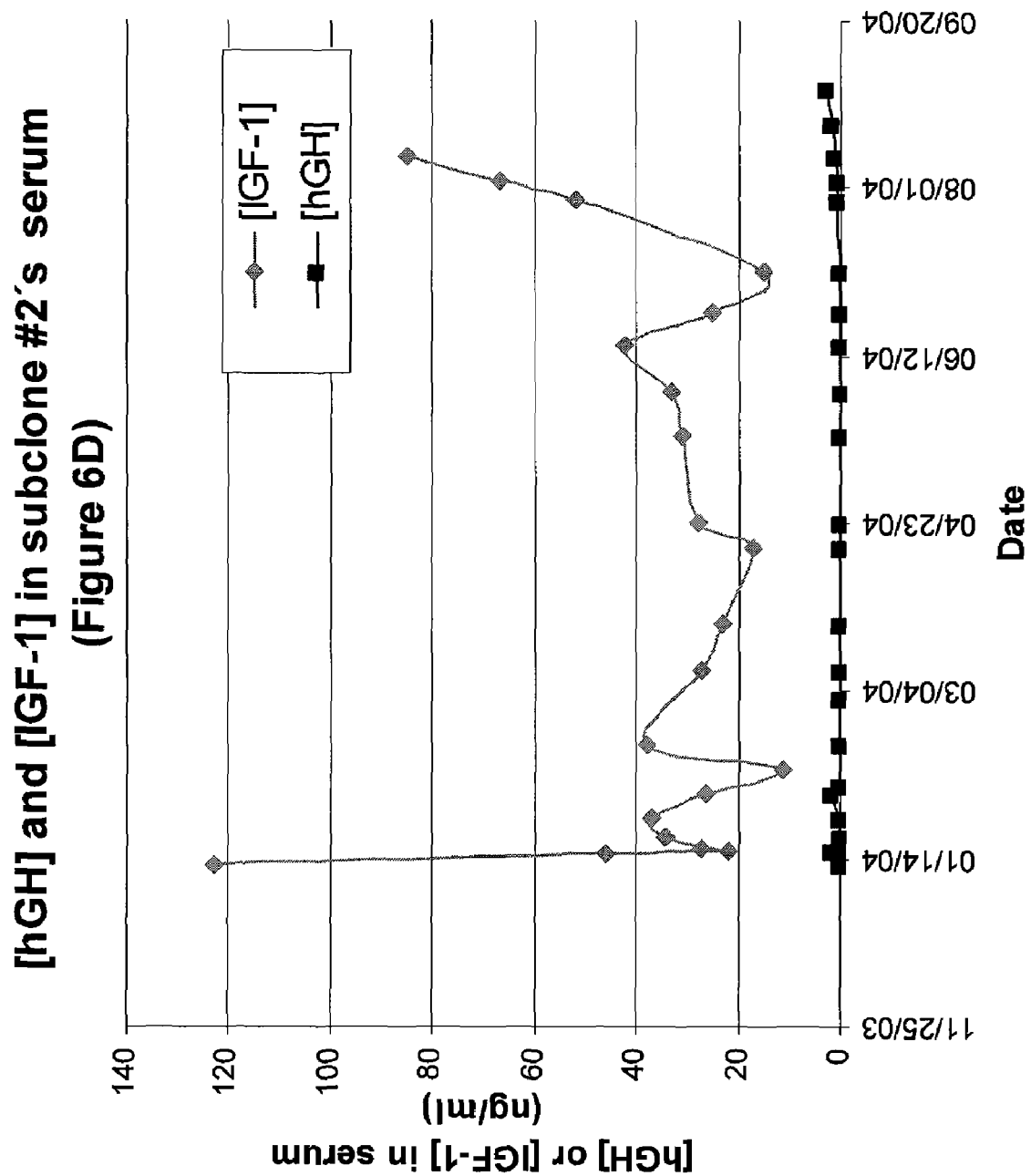

SEQUENCE LISTING

<160> NUMBER OF SEQ ID NOS: 4

<210> SEQ ID NO 1
<211> LENGTH: 31
<212> TYPE: DNA
<213> ORGANISM: Artificial
<220> FEATURE:
<223> OTHER INFORMATION: Primer PB1

<400> SEQUENCE: 1
tctactcgag gatcatctat ctgtcccaaa g                               31

<210> SEQ ID NO 2
<211> LENGTH: 27
<212> TYPE: DNA
<213> ORGANISM: Artificial
<220> FEATURE:
<223> OTHER INFORMATION: Primer PB2

<400> SEQUENCE: 2
ctaggatcca atgatctgat tttgtgg                                    27

<210> SEQ ID NO 3
<211> LENGTH: 28
<212> TYPE: DNA
<213> ORGANISM: Artificial
<220> FEATURE:

-continued

```
<223> OTHER INFORMATION: Primer PB4

<400> SEQUENCE: 3
ctaggatcca tggctacagg taagcgcc                                            28

<210> SEQ ID NO 4
<211> LENGTH: 20
<212> TYPE: DNA
<213> ORGANISM: Artificial
<220> FEATURE:
<223> OTHER INFORMATION: Primer GHTE

<400> SEQUENCE: 4
atgctgtgtc tggacgtcct                                                    20
```

PRODUCTION OF GROWTH HORMONE IN THE MILK OF A TRANSGENIC BOVINE AND METHODS OF PURIFICATION OF THE GROWTH HORMONE FROM THE MILK

This application claims the benefit of priority to U.S. Provisional Application Ser. No. 60/556,026, filed Mar. 25, 2004; U.S. Provisional Application Ser. No. 60/556,027, filed Mar. 25, 2004; U.S. Provisional Application Ser. No. 60/506,735, filed Sep. 30, 2003; and U.S. Provisional Application Ser. No. 60/506,736, filed Sep. 30, 2003, which applications are hereby incorporated by reference in their entirety.

BACKGROUND OF THE INVENTION

Protein factors and hormones involved in human health care have been currently produced by pharmaceutical industry by extraction or by recombinant technology in the last decades. Expression of genetic constructs involving the desired genes were successfully expressed in bacteria, yeast or mammalian cell lines. However, the use of mammalian cell cultures to obtain complex proteins, such as those which require a proper glycosylation pattern, involves high cost procedures.

Recombinant DNA technology has been used increasingly over the past decade for the production of commercially important biological materials. To this end, the DNA sequences encoding a variety of medically important human proteins have been cloned. These include insulin, plasminogen activator, alpha1-antitrypsin and coagulation factors VIII and IX. At present, even with the emergent recombinant DNA techniques, these proteins are usually purified from blood and tissue, an expensive and time consuming process which may carry the risk of transmitting infectious agents such as those causing AIDS and hepatitis.

Although the expression of DNA sequences in bacteria to produce the desired medically important protein looks an attractive proposition, in practice the bacteria often prove unsatisfactory as hosts because in the bacterial cell foreign proteins are unstable and are not processed correctly.

Recognizing this problem, the expression of cloned genes in mammalian tissue culture has been attempted and has in some instances proved a viable strategy. However, batch fermentation of animal cells is an expensive and technically demanding process.

There is therefore a need for a high yield, low cost process for the production of biological substances such as correctly modified eukaryotic polypeptides. The absence of agents that are infectious to humans would be an advantage in such a process.

The possibility of obtaining transgenic animals, like cattle, for a desired gene, with the aim of getting large amounts of a human protein in milk, has been of great interest to the industry. Several groups in the literature report their success on producing human serum albumin, alpha anti-trypsin, and some other examples in transgenic cows or goats.

Many experiments have been previously performed in mice or rats, and transgene expression was always preferred to be confined to the mammary glands since beta casein or lactalbumin promoters were employed, which respond only to mammary gland transcription factors in lactating females.

The expression of a heterologous protein exclusively in milk is meant to avoid undesired influence on the host animal health and provide an easy method for purification.

People are now devoted to set up several systems to improve the yield of cell transfection or selection, and choose the source of homologous fetal somatic cell to improve survival and immunity conditions of cloned animals.

On the other hand, there is enormous interest in somatic cell nuclear transfer, mainly to make possible the propagation of elite domestic animals and engineering of transgenic animals, for agricultural and biomedical purposes. Briefly, nuclear transfer (NT) involves the enucleation of a recipient oocyte, followed by the transfer of donor cell to the perivitelline space in close apposition of the recipient cytoplast, and their fusion. Development is induced artificially by chemical or physical activation. Production of cloned offspring by somatic cell nuclear transfer has been successfully attained in sheep (Campbell, K. H., et al., Nature 380:64-66 (1996), 1996; Wells, D. N., et al., Biol Reprod 57:385-393 (1997); Wilmut, I., et al, Nature 385:810-813 (1997)); goat (Baguisi, A., et al., Nat Biotechnol 17:456-461 (1999)) and in cow (Cibelli, J. B., et al., Science 280:1256-1258 (1998); Kato, Y., et al., Science 282:2095-2098 (1998); Wells, D. N., et al., Reprod Fertil Dev 10:369-378 (1998)).

There are several factors that influence the results of NT including the methods of enucleation, fusion, activation and donor-recipient cell cycle synchrony. High efficiencies in enucleation of recipient oocytes have been achieved using DNA specific vital dyes to visualize chromatin (Stice, S. L., and Keefer, C. L., Biol Reprod 48:715-719 (1993); Westhusin, M. E., et al., J Reprod Fertil 95:475-480 (1992)). Fusion of the donor cell with the recipient oocyte depends on the accuracy of cell alignment in the pulse field, contact of the donor cell with the recipient oocyte and size of the donor cells (Collas, P., et al., Anal Biochem 208:1-9 (1993)). Activation of NT reconstructed embryo has been refined and rates of development to blastocysts are equivalent to in vitro fertilized oocytes (Liu, L., et al., Mol Reprod Dev 49:298-307 (1998)).

Successful development of NT embryos has been accomplished using mature oocytes (Willadsen, S. M., Nature 320: 63-65 (1986)), zygotes (McGrath, J., and Solter, D., Dev Biol NY 4:37-55 (1985)), and cleavage-stage embryos (Tsunoda, Y., et al., J Reprod Fertil 96:275-281 (1992)) as recipient cytoplasts; however, this is dependent on the source of the donor nucleus. Compatibility of the cell cycle between the recipient cytoplasts and the donor cells is one of the important factors that influence the development of NT embryos. Appropriate synchronization is necessary to preserve the ploidy of the reconstituted embryo.

The mitotic cell cycle has the following consecutive phases: pre-replication gap ($G_1$), synthesis of DNA (S), pre-mitotic gap ($G_2$) and mitosis (M). During a single cell cycle, all genomic DNA replicates once prior to mitosis. An interphase donor nucleus transferred into an enucleate mature oocyte (metaphase II) undergoes several morphological changes. After fusion, but prior to donor nuclear envelope breakdown (NEBD), the chromosome condenses (PCC). These changes are induced by the activity of maturation/mitosis/meiosis-promoting factor (MPF) and mitogen-activated protein kinase (MAPK) (Collas, P., and Robl, J. M., Biol Reprod 45:455-465 (1991)). MPF and MAPK activities are found in all meiotic and mitotic cells and are highest at metaphase and in mammalian oocytes these high levels also induce arrest in metaphase II. Reduction of MPF and MAPK by fertilization or activation with calcium ionophore is the signal for completion of meiosis, second polar body emission, sperm nucleus decondensation and pronuclear formation.

The direct effect of NEBD and PCC on donor chromatin is dependent on the cell cycle of the donor nucleus at the time of the transfer. Diploid $G_0/G_1$ nuclei condense to form single chromatids, but tetraploid $G_2$ nuclei condense to form double chromatids. However, nuclei in S phase at the time of the transfer show a characteristic "pulverized" appearance; PCC produces extensive DNA damage. Therefore, correct ploidy can be produced by transferring a $G_1$ or $G_0$ nuclei into metaphase II oocytes at the time of activation or before. A second method is to transfer nuclei in previously activated oocyte, in S phase, in this case is possible to use a donor cell in $G_1$ $G_0$ or S phase. Because MPF and MAPK are low; the chromatin decondenses, and undergoes DNA replication without PCC and NEBD.

A third synchronization scheme has been reported in mice, where development of a live offspring was produced by embryo reconstruction using a $G_2$ or metaphase donor cell and an enucleated metaphase 2 oocyte (Cheong, H. T., et al., Biol Reprod 48:958-963 (1993); Kwon, O. Y., and Kono, T., Proc Natl Acad Sci USA 93:13010-13013 (1996)). The extrusion of a polar body from the NT reconstructed embryo was reported, resulting in single diploid embryo and a diploid polar body (Kwon, O. Y., and Kono, T., Proc Natl Acad Sci USA 93:13010-13013 (1996)). However, there is no report of polar body formation after NT into enucleated MII oocytes in cattle, sheep or pigs, suggesting differences between species in the mechanics controlling formation of intact spindles and extrusion of polar bodies.

The cell cycle stages of the donor cell and the recipient have been suggested to be also important to reprogram the donor cell nuclei. Increasing the time between donor nuclei transfer and zygotic transcription may improve nucleus reprogramming. For this reason, several authors activated the oocyte several hours after fusion (Cibelli, J. B., et al., Science 280:1256-1258 (1998); Wakayama, T., et al., Nature 394:369-374 (1998); Wells, D. N., et al., Biol Reprod 60:996-1005 (1999)). Other reports applied sequential nuclear transfer (Stice, S. L., and Keefer, C. L., Biol Reprod 48:715-719 (1993)).

An unexplored procedure to increase the time of donor nucleus reprogramming is by nuclear transfer before metaphase II. After germinal vesicle breakdown (GVBD), all the nuclei events are regulated by a substantial increase in oocyte cytosolic MPF and MAPK, which prevent reconstruction of the nuclear envelope and entrance in the S phase until fertilization or activation. Therefore, a maturing oocyte may be a universal recipient for metaphase or $G_2$ donor cell. Even $G_1$ or $G_0$ can be used as donor cells if activation induces an S phase before cell division.

When blastomeres in $G_2$ or M are used as donor cells, nuclear reprogramming is possible (Cheong, H. T., et al., Biol Reprod 48:958-963 (1993); Kwon, O. Y., and Kono, T., Proc Natl Acad Sci USA 93:13010-13013 (1996); Liu, L., et al., Mol Reprod Dev 47:255-264 (1997)). One explanation is that some factors are displaced from the chromatin as a result of chromosome condensation. In fact, for nuclear transfer, NEBD and PCC have been considered morphological signs of nucleus reprogramming. Additionally, at the time of fertilization sperm chromatin is extremely condensed, and its volume is considerably smaller than that of nuclei of somatic cells, and oocyte has the ability to remove sperm nuclear protein. Oocyte chromosomes, during sperm-oocyte fusion, are also condensed. It is possible that condensed chromatin conformation may have some biological relevance. Consequently, by mimicking this situation by metaphase nuclear transfer, a metaphase-enucleated recipient could improve NT result. However, few researchers have used this approach in domestic animals and using blastomeres as donor cells (Liu, L., et al., Mol Reprod Dev 47:255-264 (1997)).

One goal of this invention is to characterize and refine existing somatic cell nuclear transfer to a reliable and economical technique to produce genetically identical calves from adult donor cells.

SUMMARY OF THE INVENTION

The invention relates to a non-human transgenic mammal characterized by the production of unexpectedly high levels of a recombinant growth hormone in its milk. The recombinant growth hormone may be, but is not limited to, human growth hormone. The non-human transgenic mammal may be, but is not limited to, an animal of bovine species.

The invention further relates to a plasmid that provides the expression of a protein of interest in the mammary cells of mammals in which the expression is regulated by the beta casein promoter. The protein of interest may be, but is not limited to, human growth hormone.

The invention also relates to different methods of making a non-human transgenic mammal that produce a recombinant growth hormone in its milk. The recombinant growth hormone may be, but is not limited to, human growth hormone. The non-human transgenic mammal may be, but is not limited to, an animal of bovine species.

The invention also relates to a method of producing a protein of interest, comprising making a non-human transgenic mammal that produces said protein in its milk, obtaining said milk from the non-human transgenic mammal and purifying said protein of interest from the milk. The protein of interest may be, but is not limited to, human growth hormone. The non-human transgenic mammal may be, but is not limited to, an animal of bovine species.

The invention also relates to a method of producing and purifying a recombinant growth hormone from the milk of a transgenic mammal. The recombinant growth hormone may be, but is not limited to, human growth hormone. The transgenic mammal may be, but is not limited to, an animal of bovine species.

BRIEF DESCRIPTION OF THE FIGURES

FIGS. 1A-1B show the daily milk volume collected from a transgenic cow obtained by the fusion of an enucleated oocyte and a fibroblast previously transfected with a plasmid containing the gene which encodes the human growth hormone (hGH) and a promoter that directs its expression to mammary cells.

FIGS. 2A-2C show the bacteria count found in the milk collected from the same transgenic cow.

FIGS. 3A-3B show the biological activity of the hGH contained in the milk of the same transgenic cow.

FIG. 4A shows the daily mass of hGH produced in the milk of the same transgenic cow. This magnitude and the daily milk volume collected from the transgenic cow are plotted together in FIG. 4B.

FIGS. 6A and 6B show the serum concentration of hGH and insulin-like growth factor-1 (IGF-1) in two transgenic calves obtained by subcloning of a cow which is transgenic for the production of hGH in its milk. In FIGS. 6C and 6D, the time profiles of serum concentrations of hGH and IGF-1 are plotted together for each of these transgenic calves.

DETAILED DESCRIPTION OF THE INVENTION

Figure 5B:
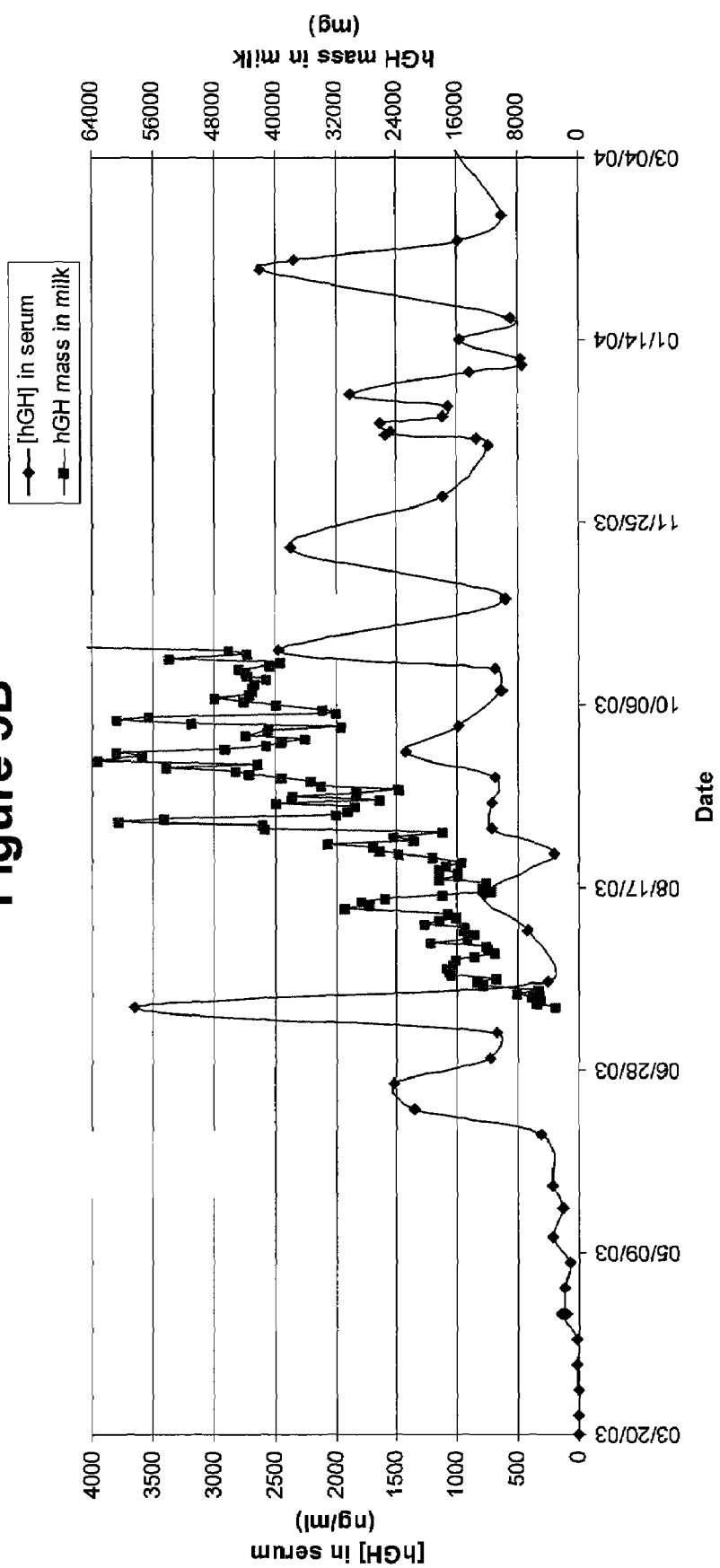
FIG. 5A shows the concentration of hGH and insulin-like growth factor-1 (IGF-1) in the serum of the same transgenic cow, and the daily mass of hGH produced in the milk of the same transgenic cow. The concentration of hGH in the transgenic cow's serum and the daily mass of hGH produced in the milk of the transgenic cow are plotted together in FIG. 5B.
In FIG. 5C, the time profiles of the transgenic cow's serum concentrations of hGH and IGF-1 are plotted together.

The invention relates to a non-human transgenic mammal characterized by the production of unexpectedly high levels of a recombinant growth hormone in its milk. This mammal may be, but is not limited to, an animal of bovine species. Other species of transgenic mammals may be, but are not limited to, porcine species, ovine species, caprine species, or rodent species.

The recombinant growth hormone can be, but is not limited to, human growth hormone. This molecule, also known as somatotropin, is a protein consisting in 191 amino acids, with a molecular weight of about 22 kD. It is essential for linear growth and its applications are well established.

The invention also relates to a transgenic mammal, characterized by the fact that the recombinant growth hormone produced in its milk self-stimulates the animal's mammary glands in order to produce more milk containing said hormone.

The invention also relates to a plasmid comprising a gene encoding a protein of interest operably linked to a beta casein promoter and a β lactamase gene. This protein of interest can be, but is not limited to, human growth hormone. This plasmid can be pRβhGH.

In a further embodiment, the plasmid additionally includes a neomycin resistance gene for selection of geneticin resistant cells. An example of such plasmid is pRNeo.

In a further embodiment, the plasmid includes the gene coding for a green fluorescent protein such as GFP, which is under control of the cytomegalovirus (CMV) promoter. An example of such a plasmid is pRNeoGreen.

The invention further relates to a plasmid such us those described above, which has been linearized by restriction digestion. In particular, use of restriction enzyme ApaLI is employed and the β lactamase gene is excised.

The plasmids pRβhGH, pRNeo and pRNeoGreen were deposited under the terms of the Budapest Treaty. The name and address of the depository are DSMZ—Deutsche Sammlung von Mikroorganisen und Zellkulturen GmbH, Mascheroder Weg 1b, 38124 Braunschweig, Germany. pRβ-hGH was deposited at the DSMZ on Oct. 1, 2004 and given DSMZ Deposit Number DSM 16763. pRNeo was deposited at the DSMZ on Oct. 1, 2004 and given DSMZ Deposit Number DSM 16764. pRNeoGreen was deposited at the DSMZ on Oct. 1, 2004 and given DSMZ Deposit Number DSM 16765.

The invention further relates to the plasmid constructed on basis of a Neo resistance gene-containing plasmid, into which a modified shorter beta casein promoter region was inserted upstream a hGH coding region, such as pVEβcashGH. A linear fragment may be obtained from the plasmid pVEβ-cashGH by excising the beta lactamase gene.

The invention further relates to a method for the transfection of genetic constructs using a combination of cationic lipids for liposome utilization.

Methods of selection of neomycin resistant cells in appropriate media are also described, as are methods of selecting green fluorescent transgenic cells. These cells are picked carefully, so as to avoid cell damage.

The invention also relates to a method of nuclear transfer of cells arrested in $G_0$, or at different times of the cell cycle, into enucleated bovine oocytes.

The invention relates to a method of transgenic embryo transfer into hormone stimulated cow uteri.

According to the invention, a method of determining animal health parameters is disclosed. Analyses are performed on both the animal's serum and milk in order to determine such parameters.

The invention further relates to a method of making a non-human transgenic mammal comprising obtaining a gene which encodes a growth hormone, cloning the gene into a plasmid whereby the gene is operably linked to a promoter that will direct the expression of the gene in mammary cells, resulting in an expression plasmid, transfecting somatic cells with the expression plasmid so that the plasmid is incorporated into the genome of the cells, resulting in transgenic somatic cells, enucleating a mature oocyte, resulting in an enucleated oocyte, fusing one transgenic somatic cell with the enucleated oocyte resulting in a monocell embryo, implanting the embryo in the uterus of a receptive mammal, and monitoring the pregnancy through the birth of the transgenic mammal.

The invention further relates to a method of making a non-human transgenic mammal comprising extracting somatic cells from a female mammal which is transgenic for the production of a recombinant growth hormone in its milk, optionally fibroblasts, enucleating a mature oocyte, resulting in an enucleated oocyte, fusing one transgenic somatic cell with the enucleated oocyte resulting in a monocell embryo, implanting the embryo in the uterus of a receptive mammal, and monitoring the pregnancy through the birth of the transgenic mammal.

The invention further relates to a method of making a non-human transgenic mammal comprising superovulating a female non-human mammal which is transgenic for the production of a recombinant growth hormone in its milk, artificially inseminating the mammal with semen obtained from a male non-human, non-transgenic mammal, to produce embryos, collecting the embryos, implanting the embryos in the uterus of a receptive mammal, and monitoring the pregnancy through the birth of the transgenic mammal.

The invention further relates to a method of making a non-human transgenic mammal comprising superovulating a female non-human mammal which is transgenic for the production of a recombinant growth hormone in its milk, artificially inseminating the mammal with semen obtained from a male non-human mammal which is transgenic for the production of said recombinant growth hormone, to produce embryos, collecting the embryos, implanting the embryos in the uterus of a receptive mammal, and monitoring the pregnancy through the birth of the transgenic mammal.

The invention further relates to a method of making a non-human transgenic mammal comprising superovulating a female non-human, non-transgenic mammal, artificially inseminating the mammal with semen obtained from a male non-human mammal which is transgenic for the production of a recombinant growth hormone, to produce embryos, collecting the embryos, implanting the embryos in the uterus of a receptive mammal, and monitoring the pregnancy through the birth of the transgenic mammal.

The recombinant growth hormone may be, but is not limited to, human growth hormone. The non-human transgenic mammal may be, but is not limited to, an animal of bovine species.

The invention further relates to a method to produce a protein comprising making a non-human transgenic mammal that produces a protein of interest in unexpectedly high yields in its milk, obtaining the milk from the non-human transgenic mammal, and purifying the protein of interest from the milk.

The invention also relates to a method to produce a protein of interest in a non-human transgenic mammal made by a process comprising obtaining a gene which encodes said protein of interest, cloning the gene into a plasmid whereby the gene is operably linked to a promoter that will direct the expression of the gene in mammary cells, resulting in an expression plasmid, transfecting somatic cells, optionally fibroblasts, with the plasmid so that the plasmid is incorporated into the genome of said somatic cells, resulting in transgenic somatic cells, enucleating a mature oocyte, resulting in an enucleated oocyte, fusing one transgenic somatic cell with the enucleated oocyte resulting in a monocell embryo, implanting the embryo in the uterus of a receptive mammal, and monitoring the pregnancy through the birth of the transgenic mammal.

The invention further also relates to a method to produce a protein of interest in a non-human transgenic mammal made by a process comprising extracting somatic cells from a female mammal which is transgenic for the production of said protein of interest in its milk, optionally fibroblasts, enucleating a mature oocyte, resulting in an enucleated oocyte, fusing one transgenic somatic cell with the enucleated oocyte resulting in a monocell embryo, implanting the embryo in the uterus of a receptive mammal, and monitoring the pregnancy through the birth of the transgenic mammal The invention also relates to a method to produce a protein of interest in a non-human transgenic mammal made by a process comprising superovulating a female non-human mammal which is transgenic for the production of said protein of interest in its milk, artificially inseminating the mammal with semen obtained from a male non-human, non-transgenic mammal, to produce embryos, collecting the embryos, implanting the embryos in the uterus of a receptive mammal, and monitoring the pregnancy through the birth of the transgenic mammal.

The invention also relates to a method to produce a protein of interest in a non-human transgenic mammal made by a process comprising superovulating a female non-human mammal which is transgenic for the production of said protein of interest in its milk, artificially inseminating the mammal with semen obtained from a male non-human mammal which is transgenic for the production of said protein of interest, to produce embryos, collecting the embryos, implanting the embryos in the uterus of a receptive mammal, and monitoring the pregnancy through the birth of the transgenic mammal.

The invention also relates to a method to produce a protein of interest in a non-human transgenic mammal made by a process comprising superovulating a female non-human, non-transgenic mammal, artificially inseminating the mammal with semen obtained from a male non-human mammal which is transgenic for the production of said protein of interest, to produce embryos, collecting the embryos, implanting the embryos in the uterus of a receptive mammal, and monitoring the pregnancy through the birth of the transgenic mammal.

The transgenic mammals characterized by the production of unexpectedly high levels of a protein of interest in their milk, can be, but are not limited to, animals of bovine species. Other species of transgenic mammals may be, but are not limited to, porcine species, ovine species, caprine species or rodent species. The protein of interest can be, but is not limited to, human growth hormone.

The invention further relates to a non-human transgenic mammal of bovine species that produces recombinant human growth hormone in its milk, whose genome comprises an integrated plasmid, said plasmid comprising the human growth hormone gene and a beta casein promoter that directs expression of said gene in mammary cells of the mammal.

The invention further relates to a transgenic mammal that produces hGH in unexpectedly high levels, yet does not show the physical growth expected with such a high level of hGH production. Since transgenic bovines are affected by the presence of human growth hormones, it would be expected that the animals would grow beyond non-transgenic growth rates, and to suffer from conditions such as diabetes mellitus, hypertension, increased risk of cardiovascular disease and enlargement of body organs, including the liver, spleen, kidneys and heart. Such high levels of hGH should render the animal, theoretically, non-viable. However, this is not the case. A mammal, such as a cow, with alarmingly high levels of a foreign hormone in its blood, but which is perfectly healthy and yields an outstanding productivity of a recombinant protein constitutes an unexpected and innovative contribution.

The recombinant human growth hormone of the invention is produced at unexpectedly high levels. The level of human growth hormone produced is greater than about 1.0 g/L milk. The level of hGH can be greater than about 2.0 g/L milk. The level of hGH produced can also be greater than about 3.0 g/L milk. In another embodiment, the level of hGH produced can be greater than about 4.0 g/L milk. In yet another embodiment, the level of hGH produced can be greater than about 5.0 g/L milk. In a further embodiment, the level of hGH produced can be greater than about 6.0 g/L milk. In yet a further embodiment, the level of hGH produced is about 1.0 g/L milk to about 7.0 g/L milk. In a further embodiment, the level of hGH produced is about 2.0 g/L milk to about 6.0 g/L milk. In yet another embodiment, the level of hGH produced is about 2.0 to about 5.0 g/L milk.

Additionally, the invention relates to a method of purifying a recombinant growth hormone from the milk of a transgenic mammal, as well as assays of said hormone. The purification methods can include chromatography and concentration steps. Different types of chromatography can be employed and include ion exchange chromatography, reverse phase chromatography, molecular exclusion chromatography or affinity chromatography. The ion exchange chromatography can be anion exchange chromatography. The affinity chromatography can be immunoaffinity chromatography. Further, multiple chromatography steps may be performed.

The invention further relates to a method of purifying a recombinant growth hormone from milk of a non-human transgenic mammal that produces a recombinant growth hormone comprising clarifying the milk of a non-human transgenic mammal, resulting in a clarified milk, and subjecting the clarified milk to chromatography, resulting in purified recombinant growth hormone.

The invention further relates to a method of purifying a recombinant growth hormone from milk of a non-human transgenic mammal that produces a recombinant growth hormone comprising clarifying the milk of a non-human transgenic mammal, resulting in a clarified milk, subjecting the clarified milk to expanded-bed anion exchange chromatography, resulting in an anion exchange chromatographed material, subjecting the anion exchange chromatographed material to reverse phase chromatography, resulting in a reverse phase chromatographed material, subjecting the reverse phase chromatographed material to anion exchange chromatography, resulting in an anion exchange chromatographed material, subjecting the anionic exchange chromatographed material to molecular exclusion chromatography, resulting in a molecular exclusion chromatographed material, concentrating the molecular exclusion chromatographed material, resulting in a concentrated material, and subjecting the concentrated material to molecular exclusion chromatography, resulting in pure recombinant growth hormone.

The invention also relates to a method of purifying a recombinant growth hormone from milk of a non-human transgenic mammal that produces a recombinant growth hormone comprising clarifying milk obtained from a transgenic mammal, resulting clarified milk, subjecting the clarified milk to immunoaffinity chromatography, resulting in an immunoaffinity chromatographed material, subjecting the immunoaffinity chromatographed material to reverse phase chromatography, resulting in a reverse phase chromatographed material, subjecting the reverse phase chromatographed material to anionic exchange chromatography, resulting in an anionic exchange chromatographed material, subjecting the anionic exchange chromatographed material to molecular exclusion chromatography, resulting in a molecular exclusion chromatographed material, subjecting the molecular exclusion chromatographed material to concentration, resulting in a concentrated material, and subjecting the concentrated material to molecular exclusion chromatography, resulting in pure recombinant growth hormone.

The recombinant growth hormone of the purification methods described above may be, but is not limited to, human growth hormone. The transgenic mammal may be, but is not limited to, a mammal of bovine species.

The following examples are illustrative, but not limiting, of the method and compositions of the present invention. Other suitable modifications and adaptations of the variety of conditions and parameters normally encountered in enzymatic production of chemicals and protein purification procedures which are obvious to those skilled in the art are within the spirit and scope of the invention.

EXAMPLE 1

Construction of Expression Plasmids

We generated a construct bearing a large portion of the bovine beta casein gene promoter, including a short fragment of the 5' non-coding beta casein gene region, fused to the coding sequence of the human growth hormone gene. The beta casein region employed in different constructs was decreased from 3.8 kbp to about 1.3 kbp. The hGH gene encompasses about 2 to 2.2 kbp depending on whether the intrinsic polyA signal is included.

The expression cassette was accommodated in the polylinker of a usual cloning vector of the pUC or pBS type.

This promoter ensures the tissue specific and developmentally regulated expression of genes under its control, like beta casein, and the heterologous hGH in this case.

The most representative plasmid is pRβhGH, which carries the full-length bovine beta casein promoter, fused to the coding sequence of the human growth hormone gene.

Other constructs disclosed are mainly derived from the original one, as depicted, to improve transfected cell selection or DNA integration efficiency into the bovine cell genome.

In the first period, co-transfection with a geneticin resistance gene-containing plasmid was performed to help selection, but next, other constructs were used, bearing NPT gene for neomycin resistance in the same vector containing the hGH expression cassette. An example of such plasmid is pRNeo.

Another plasmid for constitutive expression of green fluorescent protein was obtained, which includes the CMV promoter, an enhancer of vegetal origin (alfalfa), and the green fluorescent protein gene from the jellyfish *A. victoria*. An example of such plasmid is pRNeoGreen.

Besides, another plasmid was generated. This was constructed on basis of a Neo resistance gene-containing plasmid, into which a modified shorter beta casein promoter region was inserted upstream a hGH coding region. This plasmid is pVEβcashGH.

Other constructs were generated in which the β lactamase region was excised by ApaLI restriction and the linear fragment containing the entire expression cassette was purified after agarose gel electrophoresis, and gel extraction.

Constructs were analyzed by restriction enzymes and DNA sequencing, and their ability to conduct hGH expression was previously tested in a mammary gland cell line by fluorescent antibody recognition.

The preparation of the plasmid pVEβcashGH will be described in detail as an example of this part involving genetic constructs.

Preparation of pVEβcashGH

The aim of this construct is to provide the minimal extension of beta casein promoter region to direct specific regulated transcription of the hGH gene fused immediately downstream, along with its polyA signal in a host organism.

The use of pVEX as the original vector permits the use of neomycin resistance gene regulated by a tk promoter already present in this plasmid. The early SV40 promoter comprising 554 bp was eliminated by restriction with StuI and NdeI, and the last site filled in with Klenow, and self-ligation of the resulting vector.

Beta casein short promoter was obtained after PCR amplification of a 1.3 kbp fragment from the 3.8 kbp original gene promoter region, by using the following oligos as primers:

```
PB1
5' TCTACTCGAGGATCATCTATCTGTCCCAAAG    (SEQ ID NO: 1)
and

PB2
5' CTAGGATCCAATGATCTGATTTTGTGG        (SEQ ID NO: 2)
```

This fragment encompasses 1230 bp of the canonical promoter plus 49 bp of the first non coding exon of the beta casein gene.

The hGH gene fragment was obtained by PCR techniques on the original bovine genomic hGH clone using the following oligos as primers:

```
PB4   5'CTAGGATCCATGGCTACAGGTAAGCGCC   (SEQ ID NO: 3)
and

GHTE  5' ATGCTGTGTCTGGACGTCCT          (SEQ ID NO: 4)
```

The beta casein promoter fragment was blunted with Klenow enzyme and inserted into the BamHI filled-in site of pVEX. After selecting recombinant clones, we chose a certain direction appropriate to use the unique HindIII site located downstream in pVEX to insert the hGH coding region.

To this aim, the hGH fragment was also blunted and the plasmid HindIII site was filled in as well. Clones were selected which contain beta casein promoter and hGH properly fused to express hGH only under the control of this promoter.

The size of this plasmid is about 8.5 kbp.

Transfection of Somatic Cells

The plasmids pRβhGH (along with another plasmid with the geneticin resistance gene), pRNeo, pRNeoGreen, or pVE-βcashGH were then used for transfecting a primary culture of somatic cells, using calcium phosphate or liposome method. Fetal calf fibroblasts were generally employed to be transfected.

The transfected cells were selected adding geneticin to the culture.

After a period of 2 to 8 weeks, the cells that were resistant to geneticin were suitable for being used as donor cells to obtain transgenic clones. Transfected selected cells were analyzed by PCR to contain the expression cassette, to ensure the appropriate nuclei transfer to generate transgenic embryos.

EXAMPLE 2

Oocyte Enucleation and Metaphase Nuclear Transfer in Mature Enucleated Oocytes

Collection and In Vitro Maturation of Bovine Oocytes

Bovine oocytes were aspirated from slaughterhouse ovaries and matured in TCM-199+5% FCS at 39° C. for 24 hs. The maturation medium was equilibrated with $CO_2$ for at least 2 hours prior to use. Mature oocytes were denuded by vortexing for 2 minutes in warm TL-HEPES with 1 mg/ml bovine testis hyaluronidase.

Nuclear Transfer with Cumulus Cells

Enucleation

Oocytes were mechanically enucleated using a Narishige hydraulic micromanipulators and Nikon Diaphot microscopy. Enucleation was performed with 20 µm beveled and sharpened pipettes. Oocytes were previously stained with 5 µg/ml bisbenzimidine (Hoechst 33342[1]) dye for 20 minutes. Metaphases were enucleated by visualization of the stained chromosomes under ultraviolet light. Metaphase chromosomes were assessed after aspiration inside the pipette. A transgenic somatic cell was transferred into the perivitelline space and tightly opposed to the enucleated oocyte.

[1] Sigma Chemical Co., St. Louis, Mo., USA

Fusion

A transgenic somatic cell and an enucleated oocyte were manually aligned in the fusion chamber so that the membranes to be fused were parallel to the electrodes. This was done using a glass embryo-handling pipette.

Fusion by Electrical Means

Fusion was performed using one electrical pulse of 180 volts/cm for 15 µs (BTX Electro Cell Manipulator 200)[2] and monitored with a BTX Optimizer-Graphic Pulse Analyzer. The chamber for pulsing embryos consisted of two 0.5 mm stainless steel wire electrodes mounted 0.5 mm apart on glass microscope slide. Presumptive zygotes were monitored for fusion, lysis, and fragmentation.

[2] BTX Inc., San Diego, Calif., USA

Assessment of Developmental Competence

Zygotes were evaluated at 48 hours after fertilization for cleavage and after 7 to 9 days for development to morulae or blastocysts.

EXAMPLE 3

Cell and Embryo Culture

Different donor cells, culture systems and oocyte recipient treatments were tested in an experiment aimed at simplifying procedures and increasing embryo survival rate in a bovine cloning program. Three culture systems for reconstructed embryos were used when adult fibroblasts were used as donor cells: TCM-199+5% FCS, Menezo+5% FCS (both with VERO cells as co-culture) and SOF without co-culture but with lower $O_2$ concentration. SOF medium was also used to culture reconstructed embryos when donor cell were genetically and non-genetically modified fetal fibroblasts. Finally, when genetically modified fetal fibroblasts were used as donor cells, recipient oocytes were previously treated with roscovitine (R), to suspend meiosis and optimize recipient usability. Oocytes were aspirated from slaughterhouse ovaries and matured in TCM-199+5% FCS at 39° C. for 24 hours. For R treated group, oocytes were incubated with 25 µM R in TCM 199+5% FCS for 24 hours at 39° C. prior to the maturation. Mature oocytes were denuded by vortexing for 3 minutes in TL HEPES with 1 mg/ml bovine testis hyaluronidase. Metaphases were assessed and oocytes were enucleated by visualization with Hoechst 33342 (5 µg/ml) under UV light (<6 seconds). Adult fibroblasts from an Angus bull and fetal fibroblasts from a 45-day old Jersey female fetus were used as donor cells. Transfection with constructs containing neomycin resistance gene was performed using liposomes. After selection with geneticin for 10-15 days, donor cells at $G_0/G1$ stages were fused to enucleated oocytes by an electrical pulse. After 3 hours, activation was induced by incubation in TL-HEPES with 5 µM ionomycin for 4 min and 2 mM 6-DMAP for 3 hours. The oocytes were then washed with TL-HEPES and co-cultured in either TCM-199+5% FCS+10 g/l albumin or Menezo+2% FCS both VERO cells, or in SOF medium and atmosphere of 5% $CO_2$+5% $O_2$+90% $N_2$. Generally, two blastocysts were transferred non-surgically per recipient cow, and pregnancies at 30-35 days determined by ultrasonography. Cleavage (48 hours), development to blastocysts (days 7 to 9) were recorded and analyzed by Chi-square. Cleavage rates and development to blastocysts were higher when embryos were cultured in SOF. However, no differences were observed in pregnancy rates due to different culture conditions or source of donor cells. Suspension of meiotic maturation for 24 hours did not compromise the developmental competence of recipient oocytes. Therefore, treatment with roscovitine might be used to increase the availability of oocytes for NT procedures. See Table 1 below.

TABLE 1

| Treatment | n | Cleavage (%) | Blastocyst (%) | implanted recipient | Preg. (%) |
|---|---|---|---|---|---|
| Adult fibroblast TC199 + VERO | 294 | 156 (53.9)$^a$ | 22 (7.5)$^a$ | 13 | 5 (38.4) |
| Adult fibroblast Menezo + VERO | 324 | 236 (72.3)$^{bc}$ | 29 (8.9)$^a$ | 17 | 5 (29.4) |
| Adult fibroblast SOF | 108 | 81 (75.0)$^{bc}$ | 24 (22.2)$^b$ | 11 | 5 (45.4) |
| Fetal fibroblast SOF | 197 | 122 (61.9)$^{ab}$ | 33 (16.7)$^{ab}$ | 16 | 5 (31.6) |
| Transfected fetal fibroblast SOF | 646 | 476 (73.7)$^{bc}$ | 128 (19.8)$^b$ | 56 | 25 (44.6) |
| Transfected fetal fibroblast SOF-R | 228 | 191 (83.7)$^c$ | 51 (22.3)$^b$ | 30 | 16 (53.3) |
| Total | 1797 | 1262 (70.2) | 287 (15.9) | 143 | 61 (44.5) |

Percentages within columns with different superscripts are different (P<0.05)

The implanted cows are allowed to normally pass the pregnancy up to a natural delivery. Eventually a chirurgic approach (Caesarea) could be used for delivery. The newborns are fed with Ig rich colostrum during the first 48 hours, and then synthetic, later natural (all of them free of animal origin compounds) foods are used.

EXAMPLE 4

Tests Performed on Transgenic Calves and the Recombinant Protein Produced

In the current example, we present a full description of the tests performed on a particular transgenic calf, which was obtained as a result of the procedure described in Examples 1 to 3, and on the recombinant protein produced by it. Nonetheless, it should remain clear that the same set of assays is performed on animals that are born as a consequence of other methods for obtaining transgenic calves, such as those that will be described in Examples 5 and 6 below.

It was proved by means of PCR reactions performed on DNA purified from the calf's white blood cells, using DNA from non-transgenic jersey calves as the negative control, that bovine beta casein promoter and the hGH encoding gene are included in the transgenic calf cells genome. They can be found together as a unique DNA fragment different to the homologue beta casein gene of the animal.

It was corroborated, by using a Pharmacia automatic sequencer, that the inserted gene sequence corresponds 100% to the hGH encoding gene. It includes the introns, secretion signal and terminator. The bovine beta casein promoter that controls that same hGH gene expression in our calf was sequenced, too. All those elements coincide exactly with the expected theoretical sequence from the genetic construct used to transform the cells out of which the clones were generated.

Once known the exactitude of the genetic phase of the experiment, we passed to prove the recombinant protein produced is the expected one and coincides in every one of its physical and chemical characteristics with the natural hGH.

For this purpose, we had to obtain milk from the calf, since the beta casein promoter allows the expression of the recombinant protein only in the mammary glands, when the animal is at its milk producing time.

The transgenic calf was then induced by a hormone treatment to produce milk by the time it completed her tenth month. By that time the calf weighed 240 kg (approximately 530 lbs).

The first phase of said treatment involved the combined administration, by subcutaneous route, of estrogens (estradiol benzoate, Histeren®, Instituto Rosenbusch) and progestagens (medroxyprogesterone acetate, Pronal®, Aton), comprising 5 successive applications of each drug, in a dose of 0.1 mg/kg and 0.25 mg/kg, respectively, every 48 hours (i.e., on days 1, 3, 5, 7 and 9, assuming that the treatment commences on day 1).

The second phase comprised the administration, by subcutaneous route, of dexamethasone (Decadron, Sidus) and oxytocin (Orasthin®, Hoechst Marion Roussel); a total amount of 20 mg of the former being injected over a period comprising days 18 to 20 (a third of said total mass each day), and 3 applications of 50 IU of the latter, on days 21 to 23.

The information above is summarized in Table 2:

TABLE 2

| Day | 1 | 2 | 3 | 4 | 5 | 6 | 7 | 8 | 9 | 10 | (...) | 17 | 18 | 19 | 20 | 21 | 22 | 23 |
|---|---|---|---|---|---|---|---|---|---|---|---|---|---|---|---|---|---|---|
| Histeren (mg/kg) | 0.10 | | 0.10 | | 0.10 | | 0.10 | | 0.10 | | | | | | | | | |
| Pronal (mg/kg) | 0.25 | | 0.25 | | 0.25 | | 0.25 | | 0.25 | | | | | | | | | |
| Decadron (mg) | | | | | | | | | | | | | 6.66* | 6.66* | 6.66* | | | |
| Orasthin (IU) | | | | | | | | | | | | | | | | 50 | 50 | 50 |

*Approximately a third of the total mass (20 mg) was administered each day

As expected, the cow commenced producing colostrum the day after the treatment had finished, and then, progressively, the quality of the produced fluid turned to milk. The collected fluid was properly stored and thoroughly analyzed.

Several tests, whose results are shown in FIGS. 1-4, were performed on the colostrum and milk (for simplicity, both colostrum and milk will be hereinafter referred to as "milk", except when a distinction should be made). First, the volume of the collected milk was measured. The initial milk productivity (first five lactating days) was approximately 1,650 mL/day. During the first productive month, two manual milkings per day were performed, one in the morning and one in the afternoon (the contribution of each udder to the final volume can be noticed); whereas from the second month forth, as the production of milk started to increase, three milkings per day were performed (in the morning, at noon, and in the afternoon). The daily volumes increased in a more or less continuous way, until reaching close to the 10,000 mL three months after the first milking. Detailed information regarding this topic (FIG. 1A) can be visualized in the curve of daily milk volume vs. date (FIG. 1B).

In parallel with the measurements of milk volume, microbiological assays were performed on the milk, whose results (FIG. 2A) are shown in the corresponding plots of CFU (Colony-forming units) per ml vs date and (FIGS. 2B-2C).

Biological activity (of hGH) was also assessed by a biological activity assay in vitro in NB2 cells culture (FIGS. 3A-3B). It was proved that the biological activity of the recombinant hGH produced in the heifer's milk is within the method's error rank, at the normal values for human natural hGH. Moreover, the obtained milk was studied by Western blot, in which a main band, corresponding to intact hGH, was detected. Additional minor bands corresponding to cleaved variants and aggregates were also found, as expected in these productive systems.

With the information regarding the biological activity and the daily volumes, it was possible to calculate the daily production of hGH using Equation 1, where mhGH is the daily produced mass of hGH in milligrams; BA, the biological activity in International Units; SA, the specific activity of hGH (3 IU/mg); and V, the daily volume of collected milk. The data is shown in FIG. 4A. A plot of the daily mass of hGH is shown in FIG. 4B. In order to establish a visual correlation between the daily mass of hGH and daily volume of milk, the latter was also plotted in FIG. 4B.

$$m_{hGH} = \frac{BA}{SA \times V} \quad \text{(Eq. 1)}$$

As it can be observed from this information, the daily mass of hGH in milk and the daily volume of milk tend to augment as the cow develops (the former in a greater proportion, though), which constitutes an upward trend in the recombinant hormone productivity (grams of hGH per milk liter). It can be noticed that this productivity passed from around 2 g of hGH per liter (first milking), when the product was colostrum, to an average amount of 5 g hGH per milk liter from the second lactating month forth. Thus, an unexpectedly high yield of human growth hormone was obtained as productivity increased, in a way more or less continuous as the fluid quality turned from colostrum to milk.

Although at present the mass of hGH produced per day is outstanding indeed, it should be noted that, as the cow is not fully grown yet, the upward trend in mass of recombinant protein produced per day should continue in the future, until a maximum is reached.

In parallel with the tests performed on milk, a different set of assays were carried out on the cow's serum, whose results are shown in FIGS. 5A-5C. First, measurements of the concentration of hGH in the cow's serum were performed. The results (FIG. 5A) are plotted in a graphic together with the daily mass of hGH in milk, to allow a comparison of both magnitudes (FIG. 5B).

The reference range for GH in serum (in humans) is 0.06-5 ng/ml. Assuming a hypothetical similar range for bovines, it can be noticed that, except for the beginning, the whole curve of hGH in the transgenic cow's serum versus date lies well over the upper limit of said range. This fact notwithstanding, it must be taken into account that, although hGH and the corresponding bovine hormone (bGH) are very similar regarding their amino acid sequence and 3D-structure, the former, although fully functional, is not fully active in cattle.

Therefore, in order to assess the potential risk to the cow's health due to these high levels of hGH in its serum, measurements of serum concentration of IGF-1 (Insulin-like Growth Factor 1, also known as Somatomedin C) were performed in parallel (FIG. 5A). Growth hormone performs its functions primarily through IGF-1, which is made in the liver. Because IGF-1 mediates many of the in vivo cell division and metabolic effects of growth hormone, IGF-1 assessment is a valuable diagnostic tool for the indirect evaluation of suspected growth hormone disorders. Thus, IGF-1 represents a dependable indicator of bioavailable growth hormone. The results of these analyses are shown in FIG. 5C, together with the ones corresponding to hGH, to permit the simultaneous visualization of both magnitudes.

Moreover, IGF-1 and hGH were measured in the serum of a group of non-transgenic cows in order to have a control group and thus to establish a comparison with the data corresponding to the transgenic cow. The averages of the measurements of both proteins for the non-transgenic group and the transgenic cow are displayed in Table 3 below.

TABLE 3

| | Averages | |
|---|---|---|
| | [IGF-1] in Serum | [hGH] in serum |
| Non-transgenic | 123.40 | 0.28 |
| Transgenic | 484.02 | 656.98 |

It is worth noticing that the average serum concentration of hGH in the non-transgenic group lies within the hypothetical reference range, whereas the average for the transgenic cow is well over the upper limit of said range. Besides, it is undoubted that the average level of IGF-1 in the transgenic animal's serum is categorically higher than the one corresponding to non-transgenic cows, which constitutes a fundamental difference.

Therefore, although the high concentration of hGH in the transgenic cow's serum (which in humans is known to cause disorders with severe consequences, such as diabetes mellitus, hypertension, increased risk of cardiovascular disease and enlargement of body organs, including the liver, spleen, kidneys and heart) should render the animal, theoretically, non-viable, this would not be representing, apparently, an obstacle to its health and well being. A cow with alarmingly high levels of a foreign hormone in its blood, but which is perfectly healthy and yields an outstanding productivity of a recombinant protein constitutes an unexpected and innovative contribution.

Another innovative aspect of the present invention is that the recombinant hGH which enters the cow's bloodstream, stimulates the mammary gland to produce more milk. This effect is indirectly achieved, i.e., through the action of IGF-1. This molecule increases the blood flow through the mammary gland, providing critical precursors for the synthesis of milk fat, protein, and lactose. Thus, IGF-1 acts to direct nutrients through the blood to the cells in the udder where they aid in the production of milk. Therefore, a self-stimulating animal is attained, since the recombinant hGH produced in the milk of the transgenic cow is promoting a sustained increase in the volume of milk produced by the animal through the stimulation of its mammary gland, with the corresponding secretion of more hGH in its milk.

EXAMPLE 5

Obtaining Transgenic Calves by Subcloning

Five samples of tissue from the ear of a transgenic calf were taken employing a 1.5-mm-diameter needle, whose end had been previously beveled for this purpose. The samples were shipped under refrigeration to the laboratory in a PBS-based medium containing antibiotics and antimycotics.

Afterwards, the tissue samples were incubated for 72 hours in MEM medium with 10% bovine fetal serum and antibiotics at 39° C. and atmosphere of 5% $CO_2$ Eventually, the tissue samples were removed, and fibroblasts at the periphery of the plate were allowed to grow until confluence. Once this had been achieved, the fibroblasts were incubated for at least 5 days without changing the culture medium in order to attain their synchronization in $G_0$ stage, which was assessed by means of visualization with a microscopy.

After trypsinization, individual fibroblasts were fused with enucleated bovines oocytes according to Example 2, and embryos thus obtained were cultured in SOF medium and atmosphere of 5% $CO_2$+5% $O_2$+90% $N_2$ up to the stage of blastocyst. Afterwards, generally two blastocysts were transferred non-surgically per recipient cow, and pregnancies were determined at 30-35 days by ultrasonography.

The implanted cows are allowed to normally pass the pregnancy up to a natural delivery. Eventually a chirurgic approach (Caesarea) could be used for delivery. The newborns are fed with Ig rich colostrum during the first 48 hours, and then synthetic, later natural (all of them free of animal origin compounds) foods are used.

FIGS. 6A and 6B show measurements of serum concentration of hGH and IGF-1 performed in parallel for two of the transgenic animals obtained by subcloning of a transgenic cow, and the results of these analyses are depicted in FIGS. 6C and 6D, respectively, to permit the simultaneous visualization of both magnitudes for each animal. Since at present the calves are young, the values for both hGH and IGF-1 still lie within the respective range of reference, but it is expected that they will rise the same way they did in the transgenic cow out of which these two clones were obtained.

EXAMPLE 6

Obtaining Transgenic Calves by Artificial Insemination of a Superovulated Transgenic Cow An alternative approach for obtaining transgenic bovines will be disclosed in this example. This method comprises superovulating a transgenic cow by means of a hormonal treatment; artificially inseminating said cow; recollecting the embryos thus generated; the implantation of said embryos in surrogate cows; and the development of the pregnancy up to the birth of the animals. A description of this procedure is presented below.

Superovulation

In the morning of day 1 (i.e., the day the procedure started), 150 μg of prostaglandins (D(+)-clorprostenol, Arsaprost®, Arsa) were administered to the transgenic cow by intramuscular route. The animal was subjected to a 4-kg daily diet containing approximately 15% of proteins (before day 1, the animal had been given 2 kg of food, with the same content of proteins). In the morning of day 8, a CIDR (controlled internal drug release) device of progesterone was placed intravaginally. Besides, 50 mg of progesterone and estradiol were administered by intramuscular route. The amount of food the animal was fed rose to 6 kg/day, with the same content of proteins. Then, two intramuscular injections of FSH and LH (PLUSET®, Calier) were administered on days 12, 13 and 14 (one in the morning and the other in the afternoon). The following day (day 15), the treatment went on with the administration, by intramuscular route, of two injections of PLUSET® (one in the morning and the other in the afternoon) and two injections of 150 μg of prostaglandins each (same administration regimen). In the morning of day 16, the CIDR was removed. The total amount of PLUSET® administered throughout the superovulation phase was 350 IU.

Insemination

This phase comprised three successive administrations (the first and second, in the morning and in the afternoon of day 17, respectively, and the last, in the morning of day 18) of semen from a donor jersey bull, which had been obtained previously and kept frozen to preserve the viability of the spermatozoids.

Collection of Embryos and their Implantation in Surrogate Cows

The collection of embryos by flushing of both horns of the cow's uterus with 1 l of DMPBS (Nutricell®) took place in the morning of day 26. Immediately afterwards, two embryos were transferred non-surgically per recipient cow, and pregnancies were determined at 30-35 days by ultrasonography.

The implanted cows are allowed to normally pass the pregnancy up to a natural delivery. Eventually a chirurgic approach (Caesarea) could be used for delivery. The newborns are fed with Ig rich colostrum during the first 48 hours, and then synthetic, later natural (all of them free of animal origin compounds) foods are used.

Since the generation of biological offspring obeys Mendel's law, half of the animals being born as a consequence of the procedure described above should be transgenic, and, of these, half should be males and the other half, females. Therefore, there is a high probability of obtaining a transgenic male (founder animal), whose semen could be useful for setting up a Master Bank of jersey transgenic semen to be used for the insemination of superovulated transgenic/non-transgenic cows in order to expand the transgenic herd.

EXAMPLE 7

Purification of Recombinant hGH from Milk

Once verified the approximate molecular weight, the Western blot results and the biological activity of the recombinant hGH produced in the calf's milk are correct, an exhaustive purification process was performed, for it is imperative, when manufacturing a biopharmaceutical product, that the protein of interest should be purified to homogeneity, in order to avoid the presence of possible contaminants in said product. This process comprised the steps of: obtaining the skim of the milk by means of centrifugation and dilution of the supernatant obtained to achieve a better solubility of recombinant hGH eventually retained in the micelles of casein (clarification); and passage of this solution through an expanded-bed anionic exchange chromatography column (an alternative to this step is the employ of an immunoaffinity column, see Example 8 below); the resulting solution is subdued to a reverse phase HPLC (C4) step; fractions rich in recombinant hGH are afterwards subjected to an anionic interchange chromatography.

Purified material is desalted, concentrated and subjected to molecular exclusion chromatography. This separates by a molecular weight in order to obtain the pure recombinant hGH.

The procedure for the purification of human growth hormone (hGH) from milk comprises the following steps in order: (a) clarification (b) expanded-bed anionic exchange chromatography, (c) reverse phase chromatography, (d) anionic exchange chromatography, (e) molecular exclusion chromatography (desalting), (f) concentration and (g) molecular exclusion chromatography.

Clarification

Fresh milk was mixed with a sufficient amount of Tween 80 in order to obtain a 0.5% solution. After addition of Tween 80, 2 M Tris-HCl was added to get a pH of 7.3±0.1. Afterwards, the product was homogenized for 30 minutes, and then centrifugated at 14000 g in order to separate the fat layer. Later, the resulting solution was diluted with 0.5% Tween 80 up to a conductivity of less than, or equal to, 1500 µS/cm. The pH was adjusted to 7.3±0.1 with 2 M Tris-HCl and then the product was filtered through a 0.8 µm pore membrane and stored conveniently.

Expanded-Bed Anionic Exchange Chromatography

The material resulting from the previous step is chromatographed using an anionic exchange matrix according to the following parameters:
1. Equipment:
   A. Column:
      1) Diameter: 5 cm
      2) Bed height: 30 cm (compacted bed)
      3) Matrix:
         a. Streamline Q XL (Amersham)
         b. Volume: 600 ml
2. Solutions and buffers:
   A. 0.5 N NaOH
   B. 20% Ethanol
   C. Buffer A: 20 mM Tris.HCl, pH 7.3
   D. Buffer B: 500 mM Tris.HCl, pH 7.3
   E. Buffer C: 20 mM Tris.HCl, 150 mM NaCl, pH 7.3
   F. Buffer D: 20 mM Tris.HCl, 500 mM NaCl, pH 7.3
3. Material to be chromatographed
   A. Clarified milk.
   B. Sample conditions:
      1) Volume: 25±5 l
      2) Conductivity: ≦1500 µS/cm
      3) pH: 7.3±0.1

To equilibrate the column, 1.5 volumes of the column ("vc") (900 mL) of purified water were passed through it, at a flow of 115±5 cm/hour (descending flow). Afterwards, the following solutions or buffers in the quantities hereinafter detailed were sequentially passed through it, at an flow of 230±30 cm/hour (ascending flow): 3.0 vc (1,800 ml) of 0.5 N NaOH; 3.0 vc (1,800 ml) of purified water; 1.0 vc (600 ml) of Buffer B; and, finally, 3.0 vc (1,800 ml) of Buffer A.

Once the column was equilibrated, the material to be chromatographed was loaded. Said loading was performed at 12±3° C. and at a flow of 230±30 cm/hour. Thereafter, the elution was performed at a 115±15 cm/hour flow and at the same temperature. Firstly, a sufficient amount of Buffer A was passed through the column (ascending flow), and secondly the solutions and buffers hereinafter detailed were passed in the following order (descending flow): 1.5 vc (900 ml) of Buffer A; 2.0 vc (1,200 ml) of Buffer C; and, finally, 2.0 vc (1,200 ml) of Buffer D.

Once the step had finished, the following solutions or buffers in the quantities hereinafter detailed were sequentially passed through the column, in order to clean it: 1.5 vc (900 ml) of purified water; 1.5 vc (900 ml) of 0.5 N NaOH; 2.0 vc (1,200 ml) of purified water; 1.0 vc (600 ml) of Buffer B; 1.5 vc (900 ml) of purified water; and, finally, 1.5 vc (900 ml) of 20% Ethanol.

The selected hGH containing fractions were assayed for total proteins (by Bradford method) and for the protein of interest (by RIA), and stored at 2-8° C.

Reverse Phase Chromatography

The material resulting from the previous step is chromatographed according to the following parameters:
1. Equipment:
   A. Column:
      1) Diameter: 4 cm
      2) Bed height: 48 cm
      3) Matrix
         a. BakerBond Wide-Pore Butyl (C4) 15 µm prep LC Packing (Baker)
         b. Volume: 600 ml
2. Solutions and buffers:
   A. Mobile Phase 1 (MP1): 30 mM. $NaHCO_3$, pH 7.2: Purified water:Acetonitrile (35:55:10)
   B. Mobile Phase 2 (MP2): 30 mM $NaHCO_3$, pH 7.2: Purified water:Acetonitrile (20:10:70)
   C. 50% Methanol
3. Material to be chromatographed
   A. Pool of selected fractions resulting from the previous step.
   B. Sample conditions:
      1) Volume: 30±15 l
      2) pH: 7.3±0.3

To equilibrate the column, the following solutions or buffers in the quantities hereinafter detailed were sequentially passed through it, at a flow of less than, or equal to, 478 cm/hour: 0.3 vc (180 ml) of 50% methanol; thereafter, a gradient of 50% methanol-MP2 was applied starting from a 100:0 ratio of said solutions until a 0:100 ratio of said solutions in a total volume of 1.0 vc (600 ml) was reached; once the gradient was finished, 1.0 vc (600 ml) of MP2 was passed through the column; thereafter, a gradient of MP2-MP1 was applied starting from a 100:0 ratio of said solutions until a 0:100 ratio of said solutions in a total volume of 1.0 vc (600 ml) was reached; and, finally, 2.0 vc (1,200 ml) of MP1 were passed through the column.

Once the column was equilibrated, the material to be chromatographed was filtered through a 0.45 μm pore membrane, and loaded immediately afterwards. Said loading was performed at 20±5° C. and at a flow of less than, or equal to, 238 cm/hour. Thereafter, the elution was performed at a 478±78 cm/hour flow and at the same temperature, and the solutions and buffers hereinafter detailed were passed in the following order: 1.0 vc (600 ml) of MP1; a gradient of MP1-MP2, starting from a 65:35 ratio of said solutions until a 45:55 ratio of said solutions in a total volume of 18.0 vc (9,000 ml) was reached; 1.0 vc (600 ml) of MP1-MP2 in a 45:55 ratio; and, finally, 2.0 vc (1,200 ml) of MP2.

Once the step had finished, in order to clean the column, a gradient of MP2-50% Methanol was applied, starting from a 100:0 ratio of said solutions until a 0:100 ratio of said solutions in a total volume of 1.0 vc (600 ml) was reached; and, finally, 2.0 vc (1,200 ml) of 50% methanol were passed through the column.

The fractions resulting from this chromatography were assayed by SDS-PAGE homogeneous 20% and for the oxidized hGH, and, depending on the results, a selection was performed. Afterwards, the selected hGH containing fractions were assayed for total proteins (by Bradford method), and stored at 2-8° C.

Anionic Exchange Chromatography

The material resulting from the previous step is chromatographed using an anionic exchange matrix, as follows:
1. Equipment:
   A. Column:
      1) Diameter: 5 cm
      2) Bed height: 25 cm
      3) Matrix
         a. Source 30Q (Pharmacia)
         b. Volume: 500 ml
2. Solutions and buffers:
   A. 20% Ethanol
   B. Solution K: 0.5 N NaOH, 3M NaCl
   C. Solution L: 50 mM Tris, pH 7.50
   D. Solution M: 0.1 N HCl, 3 M NaCl
   E. Mobile Phase 3 (MP3): Solution L:Acetonitrile (70:30)
   F. Mobile Phase 4 (MP4): 50 mM Tris, 0.1 M NaCl, pH 7.50:Acetonitrile (70:30)
3. Material to be chromatographed
   A. Selected fractions resulting from the previous step.
   B. Sample conditions:
      1) Volume: 4.5±1 l
      2) pH: 7.2±0.2

To equilibrate and sanitize the column, the following solutions or buffers in the quantities hereinafter detailed were sequentially passed through it, at a flow of less than, or equal to, 183±20 cm/hour: 1.0 vc (500 ml) of purified water; 1.0 vc (500 ml) of Solution K; 1.0 vc (500 ml) of Solution L; and, finally, 1.0 vc (500 mL) of MP3.

Once the column was equilibrated, the material to be chromatographed loaded. Said loading was performed at 20±5° C. and at a flow of less than, or equal to, 183 cm/hour. Thereafter, the elution was performed at a 183±20 cm/hour flow and at the same temperature, and the solutions and buffers hereinafter detailed were passed in the following order: 1.0 vc (500 ml) of MP3; a gradient of MP3-MP4, starting from a 15:85 ratio of said solutions until a 25:75 ratio of said solutions in a total volume of 5.0 vc (2500 ml) was reached; and, finally, 2.0 vc (1000 ml) of MP4 was passed through the column.

Once the step had finished, the following solutions or buffers in the quantities hereinafter detailed were sequentially passed through the column, in order to clean it: a gradient of MP4-purified water, starting from a 100:0 ratio of said solutions until a 0:100 ratio of said solutions in a total volume of 0.5 vc (250 ml) was reached; 0.5 vc (250 ml) of purified water; a gradient of purified water-Solution K, starting from a 100:0 ratio of said solutions until a 0:100 ratio of said solutions in a total volume of 0.5 vc (250 ml) was reached; 1.0 vc (500 ml) of Solution K; a gradient of Solution K-purified water, starting from a 100:0 ratio of said solutions until a 0:100 ratio of said solutions in a total volume of 0.5 vc (250 ml) was reached; 0.5 vc (250 ml) of purified water; a gradient of purified water-Solution M, starting from a 100:0 ratio of said solutions until a 0:100 ratio of said solutions in a total volume of 0.5 vc (250 ml) was reached; 1.0 vc (500 ml) of Solution M; a gradient of Solution M-purified water, starting from a 100:0 ratio of said solutions until a 0:100 ratio of said solutions in a total volume of 0.5 vc (250 ml) was reached; 1.0 vc (500 ml) of purified water; a gradient of purified water-Solution L, starting from a 100:0 ratio of said solutions until a 0:100 ratio of said solutions in a total volume of 0.5 vc (250 ml) was reached; 0.5 vc (250 ml); 0.5 vc (250 ml) of Solution L; a gradient of Solution L-purified water, starting from a 100:0 ratio of said solutions until a 0:100 ratio of said solutions in a total volume of 0.5 vc (250 ml) was reached; and, finally, 1.5 vc (750 ml) of purified water.

The selected hGH containing fractions were assayed for total proteins (by Bradford method), and stored at 2-8° C.

Molecular Exclusion Chromatography

The material resulting from the previous step is chromatographed using a molecular exclusion matrix, as follows:
1. Equipment:
   A. Column:
      1) Diameter: 5 cm
      2) Bed height: 25 cm
      3) Matrix
         a. Cellufine GH25 (Millipore)
         b. Volume: 500 ml
2. Solutions and buffers:
   A. 0.5 N NaOH
   B. 20% Ethanol
   C. Buffer C: 150 mM $NaH_2PO_4$, pH 7.2
   D. Buffer G: 320 mM Glycine, 10 mM $NaH_2PO_4$, 0.1% Tween 80, pH 6.9
3. Material to be chromatographed
   A. Selected fractions resulting from the previous step.
   B. Sample conditions:
      1) Volume: 0.5±0.2 l
      2) pH: 7.5±0.5

To equilibrate and sanitize the column, the following solutions or buffers in the quantities hereinafter detailed were sequentially passed through it, at a flow of less than, or equal to, 180 cm/hour: 1.0 vc (500 ml) of purified water; 1.0 vc (500 ml) of 0.5 N NaOH; 0.5 vc (250 ml) of purified water; 0.5 vc (250 ml) of Buffer C; and, finally, 2.0 vc (1000 ml) of Buffer G.

Once the column was equilibrated, the material to be chromatographed was loaded. Said loading was performed at 20±5° C. and at a flow of 183±20 cm/hour. Thereafter, the elution was performed at the same flow rate and temperature, and 1.0 vc (500 ml) of Buffer G was passed through the column, as many times as the number of runs which was necessary to perform.

Once the step had finished, the following solutions or buffers in the quantities hereinafter detailed were sequentially passed through the column, in order to clean it: 0.5 vc (250 ml) of purified water; 1.0 vc (500 ml) of 0.5 N NaOH; 0.5 vc (250 ml) of purified water; 0.5 vc (250 ml) of Buffer C; 0.5 vc (250 ml) of purified water; and, finally, 1.5 vc (750 ml) of 20% ethanol.

The selected hGH containing fractions were assayed for total proteins, and stored at 2-8° C.

Concentration

The fractions resulting from the previous example were concentrated according to the conditions described below:
1. Equipment:
   A. Peristaltic pump: Watson Marlow—Cat. No. 302S
   B. Tubing: Watson Marlow—Cat. No. 902.0080.016
   C. Concentrator: Prep Scale Millipore—Cat. No. CDU F006LC
2. Solutions and buffers:
   A. 0.28% Sodium Dodecyl Sulfate (SDS)
   B. 0.06% Triton
   C. 0.125 N NaOH
   D. Buffer G: 320 mM Glycine, 10 mM $NaH_2PO_4$, 0.1% Tween 80, pH 6.9
3. Material to be processed:
   A. Selected fractions resulting from the previous example.
   B. Sample conditions:
      1) Volume: 1.0±0.5 l
      2) Conductivity: 1200±100 μS/cm
      3) pH: 6.9±0.1

The equipment was first cleaned, sanitized and equilibrated, and the following sequence of solutions and buffers were flowed through the equipment: 2 l of 0.125 N NaOH; 10 l of purified water; and, finally, 2 l of Buffer G. The equipment was then ready to be used for concentration on the selected fractions, following the usual methodology. The concentration procedure was performed until a protein concentration of 15 mg/ml (assessed by Bradford method) was reached.

The selected fractions were filtered through a 0.22 μm pore membrane, assayed for total proteins (by Bradford method), and stored at 4° C.

The conductivity and the pH of the selected fractions were 1,100-1,300 μS/cm and 6.9±0.1, respectively.

Molecular Exclusion Chromatography

The material resulting from the previous step is chromatographed using a molecular exclusion matrix, as follows:
1. Equipment:
   A. Column:
      1) Diameter: 5 cm
      2) Bed height: 92 cm
      3) Matrix
         a. Sephacryl S-200 High Resolution (Amersham Pharmacia)
         b. Volume: 1,800 ml
2. Solutions and buffers:
   A. 0.5 N NaOH
   B. 20% Ethanol
   C. Buffer H: 320 mM Glycine, 2.2 mM $NaH_2PO_4$, 1.8 mM $Na_2HPO_4$, pH 7.30
3. Material to be chromatographed
   A. Fractions selected from the previous step, concentrated
   B. Sample conditions:
      1) Volume: 40±20 ml
      2) Conductivity: 1,200±100 μS/cm
      3) pH: 7.3±0.1

To equilibrate and sanitize the column, the following solutions or buffers in the quantities hereinafter detailed were sequentially passed through it, at a flow of less than 46 cm/hour: 1.0 vc (1,800 ml) of purified water; 1.0 vc (1,800 ml) of 0.5 N NaOH; and, finally, 2.0 vc (3,600 ml) of Buffer H.

Once the column was equilibrated, the material to be chromatographed was loaded. Said loading was performed at 20±5° C. and at a flow of 46±15 cm/hour. Thereafter, the elution was performed at the same flow rate and temperature, and 1.0 vc (1,800 ml) of Buffer H was passed through the column, as many times as the number of runs which was necessary to perform.

Once the step had finished, the following solutions or buffers in the quantities hereinafter detailed were sequentially passed through the column, in order to clean it: 1.0 vc (1,800 ml) of purified water; and 1.5 vc (2,700 ml) of 20% ethanol.

The fractions containing pure hGH were aseptically filtered through a 0.22 μm pore membrane into sterile, depyrogenated plastic bottles, assayed for total proteins, and stored at −20° C.

EXAMPLE 8

Alternative Procedure for the Purification of hGH from Milk

Instead of the purification method previously described, an alternative scheme can be employed in order to purify the recombinant hGH contained in the milk. The main difference between the procedure described in Example 7 and the alternative one presented in this example is that the second step of the former involves expanded-bed anionic exchange chromatography, whereas the corresponding step of the latter entails immunoaffinity chromatography. The clarification steps of both procedures are also slightly different. Since the rest of both purification schemes are identical, only the first two steps of the alternative procedure will be described below.

Clarification

Fresh milk was mixed with a sufficient amount of Tween 80 in order to obtain a 0.5% solution. After addition of Tween 80, 1 M Tris was added to get a pH of 7.3±0.3. Afterwards, the product was homogenized for 30 minutes, and then centrifugated at 14000 g in order to separate the fat layer. Later, the resulting solution was diluted 20-fold with Buffer S (50 mM Tris.HCl, 500 mM NaCl, 0.5% Tween 80, pH 7.3), and then filtered through a 0.45 μm pore membrane and stored conveniently.

Immunoaffinity Chromatography

The material resulting from the previous step is chromatographed using an immunoaffinity interaction matrix (Affigel 10 Ester Agarose, manufactured by BioRad, with covalently attached anti-GH Monoclonal Antibodies, manufactured by Bio Sidus) according to the following parameters:
1. Equipment:
   A. Column:
      1) Diameter: 30 cm
      2) Bed height: 15 cm 3) Matrix:
   a. Affigel 10 Ester Agarose (BioRad), with covalently attached anti-GH Monoclonal Antibodies (Bio Sidus)
   b. Volume: 10 l
2. Solutions and buffers:
   A. Buffer A: 50 mM Tris.HCl, 500 mM NaCl, pH 7.2
   B. Buffer B: 100 mM Citric Acid, pH 3.0
   C. Buffer C: 150 mM $NaH_2PO_4$, pH 7.2
   D. Buffer D: 50 mM Tris.HCl, 500 mM NaCl, 500 mM Guanidine.HCl, pH 7.2
   E. Buffer E: 50 mM Tris.HCl, 500 mM NaCl, pH 7.2, 0.2% Sodium Azide, 0.1 g/l Gentamicine.
3. Material to be chromatographed
   A. Clarified milk.
   B. Sample conditions:
      1) Volume: 30-50 l
      2) Conductivity: 45±15 mS/cm
      3) pH: 7.3±0.3

To equilibrate and sanitize the column, if it had not been used in the last seven days, the following solutions or buffers in the quantities hereinafter detailed were sequentially passed through it, at a flow of less than 51 cm/hour: 1.0 volume of the column ("vc") (10 l) of Buffer A; 2.0 vc (20 l) of Buffer D; 2.0 vc (20 l) of Buffer A; 1.0 vc (10 l) of Buffer B; 2.0 vc (20 l) of Buffer C; and, finally, 1.0 vc (10 l) of Buffer A.

On the other hand, if the column had been used in the last seven days, the following solutions or buffers in the quantities hereinafter detailed were sequentially passed through it, at a flow of less than 51 cm/hour: 1.0 vc (10 l) of Buffer C; and, finally, 2.0 vc (20 l) of Buffer A.

Once the column was equilibrated, the material to be chromatographed was loaded. Said loading was performed at 5±3° C. and at a flow of less than 51 cm/hour. Thereafter, the elution was performed at a 42±9 cm/hour flow and at the same temperature, and the solutions and buffers hereinafter detailed were passed in the following order: 2.0 vc (20 l) of Buffer A; and 1.5 vc (15 l) of Buffer B.

Once the step had finished, the following solutions or buffers in the quantities hereinafter detailed were sequentially passed through the column, in order to clean it: 2.0 vc (20 l) of Buffer D; 2.0 vc (20 l) of Buffer A; and, finally, 2.0 vc (20 l) of Buffer E.

The selected hGH containing fractions were assayed for total proteins (by Bradford method) and for the protein of interest (by RIA), and stored at 4° C.

EXAMPLE 9

Quality Control of Pure Recombinant hGH

Two batches of pure recombinant hGH were subjected to a series of assays to verify that the product is indistinguishable from natural hGH. Such procedures included, but are not limited to, SDS/PAGE, Western blot, biological activity in vitro (cells nb2) and in vivo (hypophysectomized rats), peptide mapping, determination of the complete aminoacid sequence, isoelectric focusing (IEF), and reverse-phase and size exclusion HPLC analyses. The results obtained in all those assays were exactly the same for both recombinant and natural hGH, which proves that the pure recombinant hGH corresponds exactly to the natural hGH, being thus suitable for manufacturing a biopharmaceutical product.

Having now fully described the invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of producing a recombinant growth hormone comprising:
   a. making a non-human transgenic mammal of bovine species that produces a growth hormone in its milk, wherein said mammal produces increased growth hormone in its serum over a nontransgenic mammal of bovine species, and wherein said mammal is made by a process of nuclear transfer comprising:
      i) enucleating a mature bovine oocyte, resulting in an enucleated oocyte;
      ii) fusing said enucleated oocyte with a bovine somatic cell, resulting in a monocell embryo, wherein said bovine somatic cell comprises an integrated plasmid which comprises a growth hormone gene operably linked to a promoter that directs expression of said gene in mammary cells of said mammal of bovine species;
   b. obtaining said milk from said non-human transgenic mammal; and
   c. purifying said growth hormone from said milk.

2. The method according to claim 1, wherein said non-human transgenic mammal is made by a process further comprising:
   a) cloning a gene that encodes a growth hormone into a plasmid whereby said gene is operably linked to a promoter that will direct the expression of said gene in mammary cells, resulting in an expression plasmid;
   b) transfecting bovine somatic cells with said expression plasmid so that said plasmid is incorporated into the genome of said somatic cells, resulting in transgenic somatic cells;
   c) implanting said embryo of step a.ii) in the uterus of a receptive bovine mammal resulting in a pregnant mammal; and
   d) monitoring the pregnancy through the birth of the transgenic mammal.

3. The method of claim 1, wherein said promoter is a beta casein promoter, and wherein said growth hormone is human growth hormone.

4. The method of claim 2, wherein the expression plasmid is pRβhGH.

5. The method of claim 4, wherein said expression plasmid further comprises a neomycin resistance gene.

6. The method of claim 5, wherein said expression plasmid that further comprises a neomycin resistance gene is pRNeo.

7. The method of claim 1, wherein said mammal is a bovine that produces recombinant human growth hormone in its milk, whose genome comprises an integrated plasmid, wherein said plasmid comprises the human growth hormone gene and a beta casein promoter that directs expression of said gene in mammary cells of said mammal.

8. The method of claim 7, wherein said plasmid is pRβ-hGH.

9. The method of claim 8, wherein said plasmid further comprises a neomycin resistance gene.

10. The method of claim 9, wherein said plasmid that further comprises a neomycin resistance gene is pRNeo.

11. The method of claim 1, wherein said somatic cells are fibroblasts.

12. The method of claim 1, wherein said transgenic somatic cells are obtained by isolation from a female transgenic mammal of bovine species for the production of said growth hormone in its milk.

13. The method of claim 12, wherein said transgenic somatic cells are fibroblasts.

14. The method of claims 1 or 12, wherein said growth hormone is a mammalian growth hormone.

15. The method of claim 14, wherein said mammalian growth hormone is human growth hormone, bovine growth hormone, porcine growth hormone, ovine growth hormone, caprine growth hormone or rodent growth hormone.

16. The method of claim 15, wherein said mammalian growth hormone is human growth hormone.

17. The method of claim 16, wherein said mammal produces human growth hormone at a level of greater than about 1.0 g hGH/L milk, wherein said mammal's genome comprises an integrated plasmid, and wherein said plasmid comprises a human growth hormone gene operably linked to a full length beta casein promoter that directs expression of said gene in mammary cells of said mammal.

18. The method of claim 17, wherein said mammal produces human growth hormone at a level of greater than about 2.0 g hGH/L milk.

19. The method of claim 18, wherein said mammal produces human growth hormone at a level of greater than about 3.0 g hGH/L milk.

20. The method of claim 19, wherein said mammal produces human growth hormone at a level of greater than about 4.0 g hGH/L milk.

21. The method of claim 20, wherein said mammal produces human growth hormone at a level of greater than about 5.0 g hGH/L milk.

22. The method of claim 21, wherein said mammal produces human growth hormone at a level of greater than about 6.0 g hGH/L milk.

23. The method of claim 14, wherein production of said mammalian growth hormone by said mammal stimulates said mammal to produce more milk comprising said mammalian growth hormone.

24. The method of claims 1 or 12, wherein the gene encoding said growth hormone linked to a promoter that directs the expression of said gene in mammary cells is found in somatic cells and germ cells of said mammal.

25. A method of purifying a recombinant growth hormone from milk of a non-human transgenic mammal of bovine species, wherein said mammal is made by nuclear transfer using a donor cell and an oocyte of bovine species, and wherein said mammal produces increased growth hormone in its serum over a nontransgenic mammal of bovine species, comprising:
  a. clarifying the milk of a non-human transgenic mammal, resulting in a clarified milk;
  b. subjecting said clarified milk to expanded-bed anion exchange chromatography, resulting in an anion exchange chromatographed material;
  c. subjecting said anion exchange chromatographed material to reverse phase chromatography, resulting in a reverse phase chromatographed material;
  d. subjecting said reverse phase chromatographed material to anion exchange chromatography, resulting in an anion exchange chromatographed material;
  e. subjecting said anionic exchange chromatographed material to molecular exclusion chromatography, resulting in a molecular exclusion chromatographed material;
  f. concentrating said molecular exclusion chromatographed material, resulting in a concentrated material; and
  g. subjecting said concentrated material to molecular exclusion chromatography, resulting in pure recombinant growth hormone.

26. The method of claim 25, wherein said growth hormone is a mammalian growth hormone.

27. The method of claim 26, wherein said mammalian growth hormone is human growth hormone, bovine growth hormone, porcine growth hormone, ovine growth hormone, caprine growth hormone or rodent growth hormone.

28. The method of claim 27, wherein said mammalian growth hormone is human growth hormone.

29. The method of claim 28, wherein said mammal produces human growth hormone at a level of greater than about 1.0 g hGH/L milk, wherein said mammal's genome comprises an integrated plasmid, and wherein said plasmid comprises a human growth hormone gene operably linked to a full length beta casein promoter that directs expression of said gene in mammary cells of said mammal.

30. The method of claim 29, wherein said mammal produces human growth hormone at a level of greater than about 2.0 g hGH/L milk.

31. The method of claim 30, wherein said mammal produces human growth hormone at a level of greater than about 3.0 g hGH/L milk.

32. The method of claim 31, wherein said mammal produces human growth hormone at a level of greater than about 4.0 g hGH/L milk.

33. The method of claim 32, wherein said mammal produces human growth hormone at a level of greater than about 5.0 g hGH/L milk.

34. The method of claim 33, wherein said mammal produces human growth hormone at a level of greater than about 6.0 g hGH/L milk.

* * * * *